United States Patent
Namai

(10) Patent No.: US 9,557,641 B2
(45) Date of Patent: Jan. 31, 2017

(54) PHOTORESIST COMPOSITION, RESIST PATTERN-FORMING METHOD, ACID DIFFUSION CONTROL AGENT, AND COMPOUND

(71) Applicant: JSR CORPORATION, Minato-ku (JP)

(72) Inventor: Hayato Namai, Tokyo (JP)

(73) Assignee: JSR CORPORATION, Minato-ku (JP)

( * ) Notice: Subject to any disclaimer, the term of this patent is extended or adjusted under 35 U.S.C. 154(b) by 137 days.

(21) Appl. No.: 14/486,532

(22) Filed: Sep. 15, 2014

(65) Prior Publication Data

US 2015/0004544 A1  Jan. 1, 2015
US 2015/0309406 A9  Oct. 29, 2015

Related U.S. Application Data

(63) Continuation of application No. PCT/JP2013/056543, filed on Mar. 8, 2013.

(30) Foreign Application Priority Data

Mar. 14, 2012 (JP) ................................ 2012-058033

(51) Int. Cl.

| G03F 7/004 | (2006.01) |
|---|---|
| G03F 7/038 | (2006.01) |
| C07D 211/46 | (2006.01) |
| G03F 7/039 | (2006.01) |
| G03F 7/11 | (2006.01) |
| G03F 7/20 | (2006.01) |
| G03F 7/30 | (2006.01) |

(52) U.S. Cl.
CPC ............. G03F 7/038 (2013.01); C07D 211/46 (2013.01); G03F 7/0045 (2013.01); G03F 7/0046 (2013.01); G03F 7/0388 (2013.01); G03F 7/0397 (2013.01); G03F 7/11 (2013.01); G03F 7/2041 (2013.01); G03F 7/30 (2013.01)

(58) Field of Classification Search
CPC ...... G03F 7/004; G03F 7/0045; G03F 7/0046; G03F 7/038; G03F 7/0388; G03F 7/0397; G03F 7/11; G03F 7/2041; G03F 7/30; C07D 211/00; C07D 211/46
USPC ..... 430/270.1, 913, 322, 919, 920; 546/203, 546/242; 560/157
See application file for complete search history.

(56) References Cited

U.S. PATENT DOCUMENTS

| 2012/0052441 A1* | 3/2012 | Sagehashi | C07D 233/60 430/270.1 |
|---|---|---|---|
| 2012/0214099 A1* | 8/2012 | Chen | G03F 7/0382 430/283.1 |
| 2012/0282548 A1* | 11/2012 | Enomoto | G03F 7/0045 430/284.1 |

FOREIGN PATENT DOCUMENTS

| JP | 5-501569 | 3/1993 |
|---|---|---|
| JP | 2001-215689 | 8/2001 |
| JP | 2006-227632 | 8/2006 |
| JP | 2006-321770 | 11/2006 |
| JP | 2009-199021 | 9/2009 |
| JP | 2011048175 A * | 3/2011 |
| JP | 2011-141494 | 7/2011 |
| JP | 2011-141495 | 7/2011 |
| JP | 2011-227454 | 11/2011 |
| JP | 2012-144666 | 8/2012 |
| JP | 2013-68777 A | 4/2013 |
| WO | 2005/069076 | 7/2005 |
| WO | 2006/035790 | 4/2006 |
| WO | 2011/007780 | 1/2011 |

OTHER PUBLICATIONS

Machine translation of JP 2011-048175.*
(Continued)

*Primary Examiner* — Amanda C Walke
(74) *Attorney, Agent, or Firm* — Oblon, McClelland, Maier & Neustadt, L.L.P.

(57) ABSTRACT

A photoresist composition containing: a polymer including an acid-labile group; a radiation-sensitive acid generator; and an acid diffusion control agent that contains a compound represented by a formula (1). In the formula (1), $R^1$, $R^2$ and $R^3$ each independently represent a hydrogen atom or a monovalent hydrocarbon group having 1 to 10 carbon atoms. A represents a group having a valency of n that is obtained by combining: a hydrogen atom, a linear hydrocarbon group having 1 to 30 carbon atoms, an alicyclic hydrocarbon group having 3 to 30 carbon atoms or a combination thereof; —O—, —CO—, —COO—, —SO$_2$O—, —NRSO$_2$—, —NRSO$_2$O—, —NRCO— or a combination thereof; and n nitrogen atoms as a binding site to the carbonyl group in the formula (1), in which a sum of atomic masses of the atoms constituting A is no less than 120. n is an integer of 1 to 4.

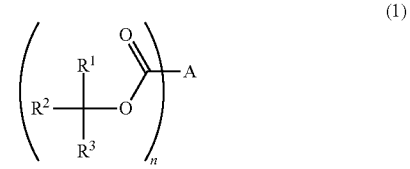

(1)

18 Claims, No Drawings

(56) References Cited

OTHER PUBLICATIONS

Office Action and Search Report issued on Jul. 6, 2016 in the corresponding Taiwanese Patent Application No. 102108443 (with English Translation).
Japanese Office Action issued Jun. 16, 2016 in Patent Application No. 2014-504844 (with English translation).
International Search Report issued Apr. 2, 2013 in PCT/JP2013/056543 filed Mar. 8, 2013.

* cited by examiner

PHOTORESIST COMPOSITION, RESIST PATTERN-FORMING METHOD, ACID DIFFUSION CONTROL AGENT, AND COMPOUND

TECHNICAL FIELD

The present invention relates to a photoresist composition, a resist pattern-forming method, an acid diffusion control agent, and a compound.

BACKGROUND ART

In chemically amplified photoresist compositions, an acid is generated from an acid generating agent upon irradiation with an exposure light such as an ArF excimer laser beam and a KrF excimer laser beam at a light-exposed site, and a reaction catalyzed by the acid allows the difference in dissolution rates in a developer solution to be produced between the light-exposed site and a light-unexposed site, thereby enabling a resist pattern to be formed on a substrate.

Along with miniaturization in processing techniques, such photoresist compositions are required not only to exhibit a superior resolving ability, but also to be superior in a line width roughness (LWR) performance, which is indicative of a variation in the line width of a resist pattern. To address the demand, incorporation of an acid diffusion control agent into the photoresist compositions is employed for the purpose of properly controlling the diffusion of the acid generated from the acid generating agent. In order to improve various performances of the photoresist compositions, various acid diffusion control agents having a specific structure have been investigated (see Japanese Unexamined Patent Application, Publication No. 2001-215689; PCT International Publication No. WO 2011/007780; Japanese Unexamined Patent Application, Publication Nos. 2009-199021, 2006-321770, 2011-141494, and 2011-141495).

Under such circumstances, in these days when further miniaturization of resist patterns is advancing, it is also demanded to further improve the resolving ability, the LWR performance, and the like, and to increase a depth of focus for the purpose of improving process stability. In addition, in the case of the aforementioned conventional acid diffusion control agents, since the resist pattern formed tends to exhibit a top loss phenomenon and the like, an improvement of the cross-sectional shape of the resist pattern is also demanded. However, the aforementioned conventional photoresist compositions are incapable of meeting these demands.

SUMMARY OF THE INVENTION

Problems to be Solved by the Invention

The present invention was made in view of the foregoing circumstances, and it is an object of the present invention to provide a photoresist composition that leads to a superior rectangularity of a cross-sectional shape, a superior LWR performance, a superior resolving ability and a favorable depth of focus.

Means for Solving the Problems

According to an aspect of the invention made for solving the aforementioned problems, a photoresist composition is provided, containing:

a polymer including an acid-labile group (hereinafter, may be also referred to as "(A) polymer" or "polymer (A)"), a radiation-sensitive acid generator (hereinafter, may be also referred to as "(B) acid generator" or "acid generator (B)"), and an acid diffusion control agent (hereinafter, may be also referred to as "(C) acid diffusion control agent" or "acid diffusion control agent (C)"), the acid diffusion control agent containing a compound represented by the following formula (1) (hereinafter, may be also referred to as "compound (I)"):

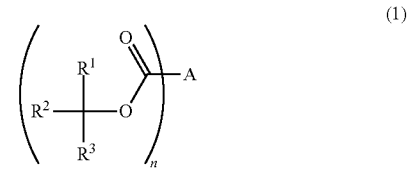

wherein in the formula (1), $R^1$, $R^2$ and $R^3$ each independently represent a hydrogen atom or a monovalent hydrocarbon group having 1 to 10 carbon atoms, wherein in a case where the monovalent hydrocarbon group is present in a plurality of number, at least two of these hydrocarbon groups optionally taken together represent a ring structure by binding with each other, together with the carbon atom to which the at least two of these hydrocarbon groups bond; A represents a group having a valency of n that is obtained by combining: at least one group selected from the group consisting of a hydrogen atom, a linear hydrocarbon group having 1 to 30 carbon atoms and an alicyclic hydrocarbon group having 3 to 30 carbon atoms; at least one group selected from the group consisting of —O—, —CO—, —COO—, —SO$_2$O—, —NR—, —NRSO$_2$—, —NRSO$_2$O— and —NRCO—; and n nitrogen atoms as a binding site to the carbonyl group in the above formula (1), wherein a sum of atomic masses of the atoms constituting A is no less than 120, wherein a part or all of hydrogen atoms included in the linear hydrocarbon group and the alicyclic hydrocarbon group are unsubstituted or substituted with a fluorine atom-free group, and wherein R represents a hydrogen atom or a monovalent hydrocarbon group having 1 to 10 carbon atoms; and n is an integer of 1 to 4.

Since the photoresist composition according to the aspect of the present invention contains the acid diffusion control agent (C) and the acid diffusion control agent (C) contains the compound (1) that has the specific structure, the photoresist composition is superior in rectangularity of a cross-sectional shape, an LWR performance, a resolving ability and a depth of focus. The compound (1) includes a carbamate group. The carbamate group is degraded by an action of an acid generated from the acid generator and the like upon an exposure, and generates a nitrogen atom-containing group. Therefore, the acid diffusion control agent (C) exhibits an excellent acid diffusion controlling function at a light-exposed site, and consequently exhibits superior storage stability. After the degradation of the carbamate group, the compound (1) has been converted to a compound that includes the specific polar group and a nitrogen atom-containing group having a molecular weight falling within a specific range (i.e., a sum of the total atomic mass of the group A and n). Therefore, the compound derived from the compound (1) after the degradation has low volatility and a high affinity to a component, e.g., the polymer, in the photoresist composition. As a result, for example, even after PEB, the compound derived from the compound (1) after the degradation is uniformly distributed in an altitude direction of a resist film formed from the photoresist composition, leading to the suppression of the top loss phenomenon and the like, thereby enabling the formation of a resist pattern exhibiting superior rectangularity of a cross-sectional shape. In addition, it is presumed that when the compound (1) exhibits the aforementioned characteristics, the diffusion of the acid diffusion control agent (C) itself can be inhibited; as a result, the photoresist composition can exhibit a superior LWR performance, a superior resolving ability and a favorable depth of focus.

It is preferred that the compound represented by the above formula (1) is represented by the following formula (2) (hereinafter, the compound represented by the following formula (2) may be also referred to as "compound (2)"):

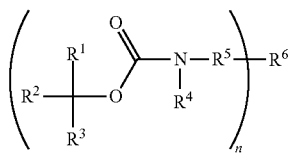

(2)

wherein in the formula (2), $R^1$, $R^2$, $R^3$ and n are as defined in the above formula (1); $R^4$ represents a hydrogen atom or a monovalent hydrocarbon group having 1 to 10 carbon atoms; $R^5$ represents a divalent hydrocarbon group having 1 to 10 carbon atoms, wherein $R^4$ and $R^5$ optionally taken together represent an alicyclic structure by binding with each other, together with the nitrogen atom to which $R^4$ and $R^5$ bond; $R^6$ represents a group having a valency of n that is obtained by combining: at least one group selected from the group consisting of a hydrogen atom, a linear hydrocarbon group having 1 to 30 carbon atoms and an alicyclic hydrocarbon group having 3 to 30 carbon atoms; and at least one group selected from the group consisting of —O—, —CO—, —COO—, —SO$_2$O—, —NR—, —NRSO$_2$—, —NRSO$_2$O— and —NRCO—, wherein a part or all of hydrogen atoms included in the linear hydrocarbon group and the alicyclic hydrocarbon group are unsubstituted or substituted with a fluorine atom-free group, wherein R represents a hydrogen atom or a monovalent hydrocarbon group having 1 to 10 carbon atoms, and wherein in the formula (2), a value obtained by the formula of: $\{(F^4+F^5+F^N) \times n + F^6\}$ is no less than 120, wherein $F^4$ represents a formula mass of $R^4$, $F^5$ represents a formula mass of $R^5$, $F^N$ represents an atomic mass of nitrogen, and $F^6$ represents a formula mass of $R^6$.

When the acid diffusion control agent (C) has the specific structure, the basicity of the nitrogen atom-containing group generated from the compound (1) can be increased, and the photoresist composition may lead to an improvement of the rectangularity of a cross-sectional shape, the LWR performance, the resolving ability and the depth of focus.

It is preferred that the compound represented by the above formula (2) is represented by the following formula (3) (hereinafter, the compound represented by the following formula (3) may be also referred to as "compound (3)"):

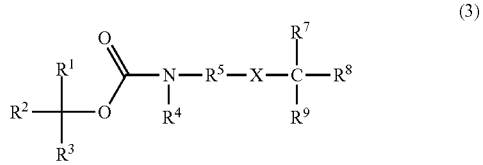

(3)

wherein in the formula (3), $R^1$ to $R^5$ are as defined in the above formula (2); $R^7$, $R^8$ and $R^9$ each independently represent at least one group selected from the group consisting of a hydrogen atom, a linear hydrocarbon group having 1 to 30 carbon atoms and an alicyclic hydrocarbon group having 3 to 30 carbon atoms, or a group that is obtained by combining: the at least one group selected from the group consisting of a hydrogen atom, a linear hydrocarbon group having 1 to 30 carbon atoms and an alicyclic hydrocarbon group having 3 to 30 carbon atoms; and at least one group selected from the group consisting of —O—, —CO—, —COO—, —SO$_2$O—, —NR—, —NRSO$_2$—, —NRSO$_2$O— and —NRCO—, wherein at least two of $R^7$, $R^8$ and $R^9$ optionally taken together represent a ring structure by binding with each other, together with the carbon atom to which the at least two of $R^7$, $R^8$ and $R^9$ bond; and X represents —O—, —CO—, —COO—, —SO$_2$O—, —NR—, —NRSO$_2$—, —NRSO$_2$O— or —NRCO—, and wherein a sum of formula masses of $R^4$, $R^5$, X, $R^7$, $R^8$ and $R^9$ and atomic masses of the nitrogen and the carbon in the formula (3) is no less than 120.

According to the photoresist composition, when the acid diffusion control agent (C) has the specific structure, the rectangularity of a cross-sectional shape, the LWR performance, the resolving ability and the depth of focus may be further improved. Moreover, the compound having the specific structure can be easily synthesized from a well-known compound that functions as an acid diffusion control agent through a reaction for forming the functional group X.

It is preferred that the photoresist composition further contains (D) an acid diffusion controller other than the acid diffusion control agent (C).

According to the photoresist composition, when the acid diffusion control agent (C) and the acid diffusion control agent other than the acid diffusion control agent (C) are used in combination, the rectangularity of a cross-sectional shape, the LWR performance, the resolving ability and the depth of focus may be improved.

According to another aspect of the present invention, a resist pattern-forming method is provided, including:
providing a resist film using the photoresist composition according to the aspect of the present invention;
exposing the resist film; and
developing the resist film exposed.

According to the resist pattern-forming method, since the aforementioned photoresist composition is used, a resist pattern can be formed that exhibits superior rectangularity of a cross-sectional shape, decreased LWR and a superior resolving ability, while attaining a greater depth of focus.

According to still another aspect of the present invention, an acid diffusion control agent contains the compound (1).

In the acid diffusion control agent, it is preferred that the compound represented by the above formula (1) is represented by the above formula (2), and it is more preferred that the compound represented by the above formula (2) is represented by the above formula (3).

Since the acid diffusion control agent contains the compound having the specific structure, the acid diffusion control agent may be suitably used as an acid diffusion control agent component of the photoresist composition, and enables the photoresist composition to lead to an improvement of the rectangularity of a cross-sectional shape, the LWR performance, the resolving ability and the depth of focus.

According to yet still another aspect of the present invention, a compound (hereinafter, may be also referred to as "compound (i)") is represented by the following formula (3):

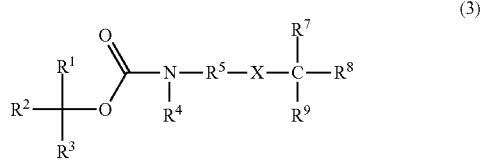

wherein in the formula (3), $R^1$, $R^2$ and $R^3$ each independently represent a hydrogen atom or a monovalent hydrocarbon group having 1 to 10 carbon atoms, wherein in a case where the monovalent hydrocarbon group is present in a plurality of number, at least two of these hydrocarbon groups optionally taken together represent a ring structure by binding with each other, together with the carbon atom to which the at least two of these hydrocarbon groups bond; $R^4$ represents a hydrogen atom or a monovalent hydrocarbon group having 1 to 10 carbon atoms; $R^5$ represents a divalent hydrocarbon group having 1 to 10 carbon atoms, wherein $R^4$ and $R^5$ optionally taken together represent an alicyclic structure by binding with each other, together with the nitrogen atom to which $R^4$ and $R^5$ bond; $R^7$, $R^8$ and $R^9$ each independently represent at least one group selected from the group consisting of a hydrogen atom, a linear hydrocarbon group having 1 to 30 carbon atoms and an alicyclic hydrocarbon group having 3 to 30 carbon atoms, or a group that is obtained by combining: the at least one group selected from the group consisting of a hydrogen atom, a linear hydrocarbon group having 1 to 30 carbon atoms and an alicyclic hydrocarbon group having 3 to 30 carbon atoms; and at least one group selected from the group consisting of —O—, —CO—, —COO—, —SO$_2$O—, —NR—, —NRSO$_2$—, —NRSO$_2$O— and —NRCO—, wherein at least two of $R^7$, $R^8$ and $R^9$ optionally taken together represent a ring structure by binding with each other, together with the carbon atom to which the at least two of $R^7$, $R^8$ and $R^9$ bond; and X represents —O—, —CO—, —COO—, —SO$_2$O—, —NR—, —NRSO$_2$—, —NRSO$_2$O— or —NRCO—, and wherein a sum of formula masses of $R^4$, $R^5$, X, $R^7$, $R^8$ and $R^9$ and atomic masses of the nitrogen and the carbon in the formula (3) is no less than 120.

Since the compound (i) has the specific structure, it may be suitably used as, e.g., an acid diffusion control agent component of a photoresist composition, and enables the rectangularity of a cross-sectional shape, the LWR performance, the resolving ability and the depth of focus to be improved. Moreover, the compound (i) can be easily synthesized from a well-known acid diffusion control agent.

"Organic group" as referred to herein means a group having at least one carbon atom.

Effects of the Invention

As explained in the foregoing, the photoresist composition and the resist pattern-forming method using the photoresist composition according to the aspects of the present invention enable a resist pattern to be formed that exhibits superior rectangularity of a cross-sectional shape, decreased LWR and a superior resolving ability, while attaining a greater depth of focus. The acid diffusion control agent according to the still another aspect of the present invention can be suitably used as an acid diffusion control agent component of the photoresist composition. Moreover, the compound according to the aspect of the yet still another present invention can be suitably used as the acid diffusion control agent. Therefore, there can be suitably used in pattern formation involved in the production of semiconductor devices, in which further progress of miniaturization is expected in the future.

DESCRIPTION OF EMBODIMENTS

Photoresist Composition

A photoresist composition according to an embodiment of the present invention contains (A) a polymer, (B) an acid generator and (C) an acid diffusion control agent. The photoresist composition may further contain, in addition to these components, (D) an acid diffusion control agent other than the acid diffusion control agent (C) (hereinafter, may be also referred to as "(D) other acid diffusion controller" or "other acid diffusion controller (D)"), (E) a fluorine atom-containing polymer and (F) a solvent, each as a favorable component, and may contain other optional component(s) within a range not leading to impairment of the effects of the present invention. Hereinafter, each component will be explained.

(A) Polymer

The polymer (A) includes an acid-labile group. The polymer (A) preferably further includes, in addition to a structural unit that includes an acid-labile group (hereinafter, may be also referred to as "structural unit (I)"), a structural unit (II) that includes at least one structure selected from the group consisting of a lactone structure, a cyclic carbonate structure and a sultone structure, and the polymer (A) may further include other structural unit such as a structural unit that includes a polar group. The polymer (A) may include one, or two or more types of each structural unit. Hereinafter, each structural unit will be explained.

Structural Unit (I)

The structural unit (I) includes an acid-labile group. The structural unit (I) is exemplified by a structural unit (I-1) represented by the following formula (4), and the like.

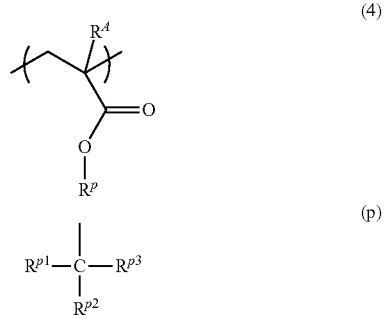

In the above formula (4), $R^A$ represents a hydrogen atom, a fluorine atom, a methyl group or a trifluoromethyl group; and RP represents a monovalent acid-labile group represented by the above formula (p).

In the above formula (p), $R^{p1}$, $R^{p2}$ and $R^{p3}$ each independently represent an alkyl group having 1 to 4 carbon atoms or a cycloalkyl group having 4 to 20 carbon atoms, wherein $R^{p2}$ and $R^{p3}$ optionally taken together represent a cycloalkanediyl group having 4 to 20 carbon atoms by binding with each other, together with the carbon atom to which $R^{p2}$ and $R^{p3}$ bond.

Structural units represented by the following formulae (4-1) to (4-4) are preferred as the structural unit (I-1).

(4-1)
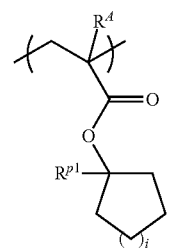

(4-2)
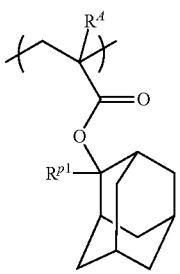

(4-3)
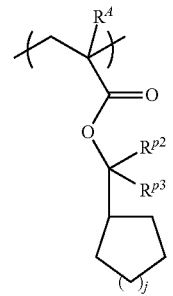

(4-4)
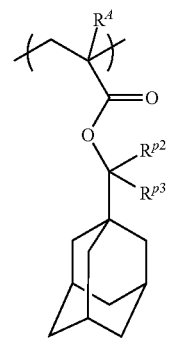

In the above formulae (4-1) to (4-4), $R^A$ is as defined in the above formula (4); $R^{p1}$, $R^{p2}$ and $R^{p3}$ are as defined in the above formula (p); and i and j are each independently an integer of 1 to 4.

The structural units represented by the above formulae (4-1) to (4-4) are exemplified by structural units represented by the following formulae, and the like.

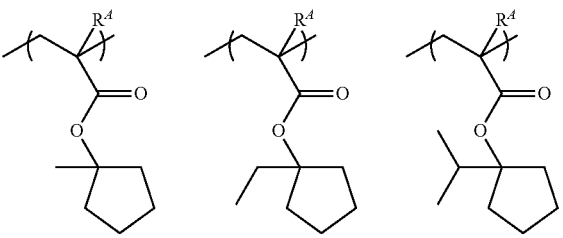

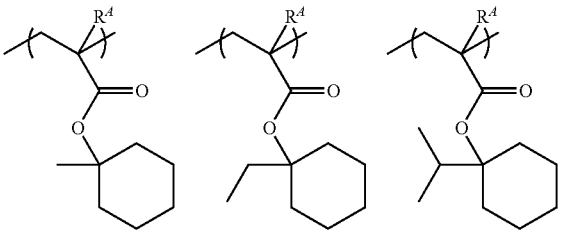

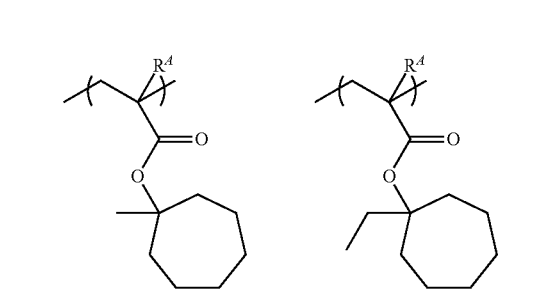

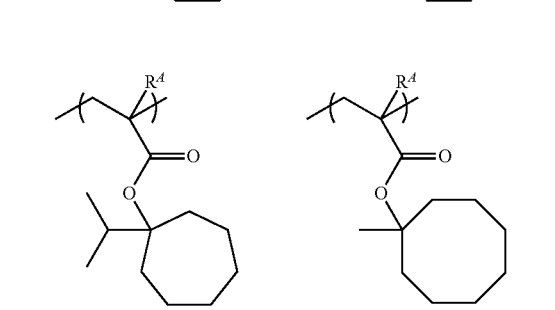

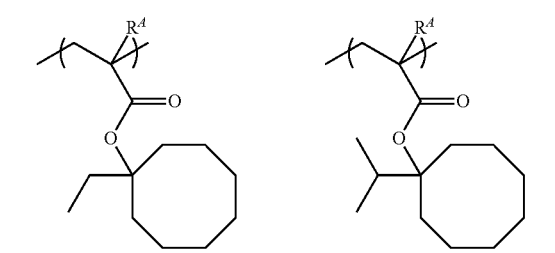

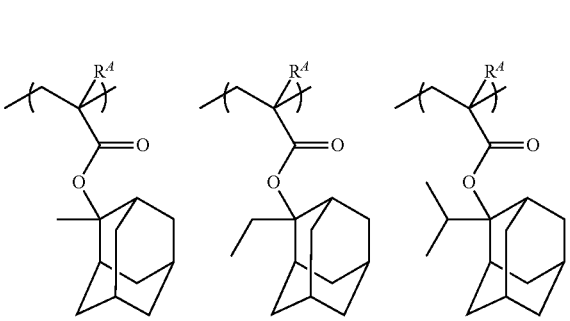

-continued

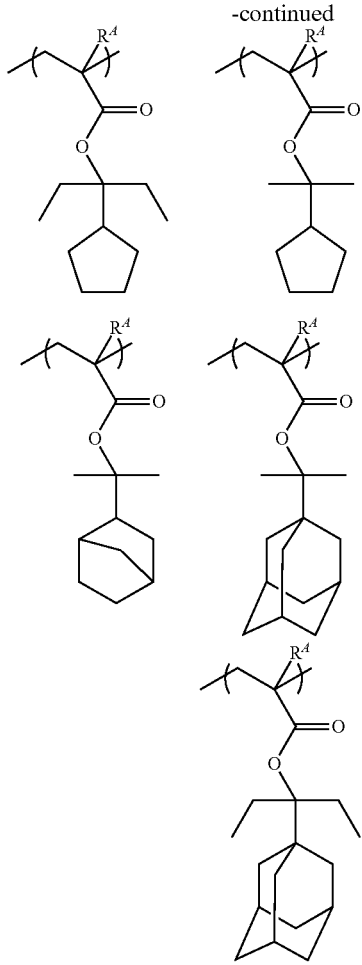
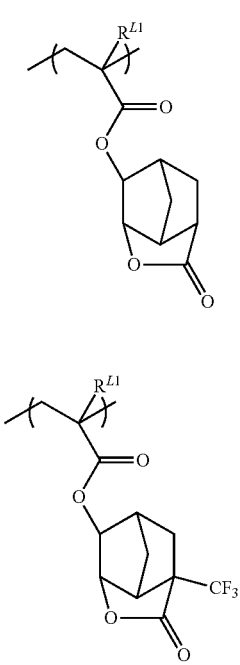
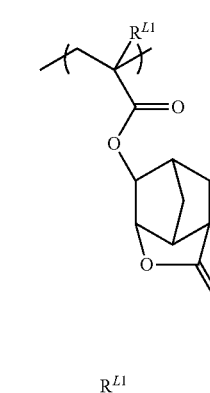
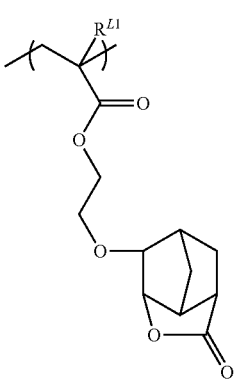
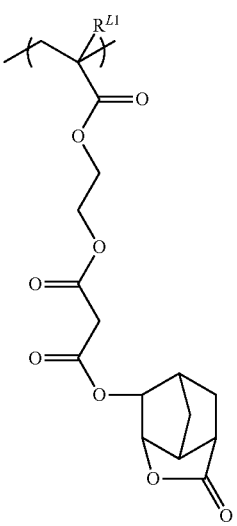

In the above formulae, $R^A$ is as defined in the above formula (4).

The structural unit (I) is preferably the structural unit represented by the above formula (4-1) or the structural unit represented by the formula (4-2), more preferably a structural unit derived from 1-alkyl-1-cyclopentyl (meth)acrylate or a structural unit derived from 2-alkyl-2-adamantyl (meth) acrylate, and still more preferably a structural unit derived from 1-ethyl-1-cyclopentyl (meth)acrylate or a structural unit derived from 2-ethyl-2-adamantyl (meth)acrylate.

The proportion of the structural unit (I) with respect to the total structural units constituting the polymer (A) is preferably 10 mol % to 100 mol %, more preferably 20 mol % to 80 mol %, and still more preferably 30 mol % to 70 mol %. When the proportion of the structural unit (I) is less than the lower limit, the pattern formability of the photoresist composition may be deteriorated.

Structural Unit (II)

The structural unit (II) includes at least one structure selected from the group consisting of a lactone structure, a cyclic carbonate structure and a sultone structure. When the polymer (A) further includes the structural unit (II), the solubility thereof in a developer solution may be adjusted. In addition, the adhesiveness of a resist pattern formed from the photoresist composition to a substrate may be improved.

The structural unit (II) is exemplified by structural units represented by the following formulae, and the like.

-continued
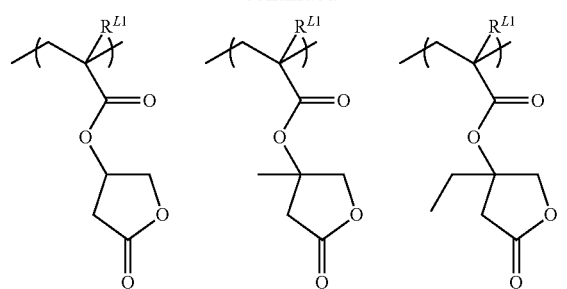
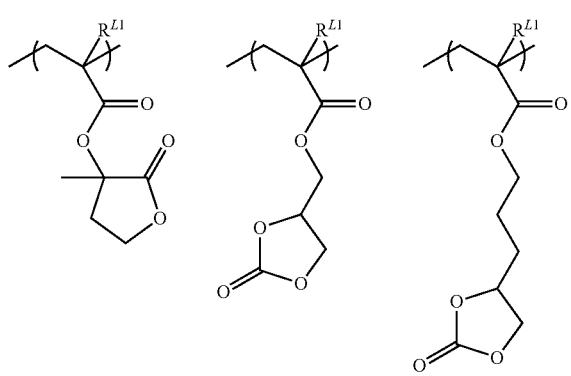
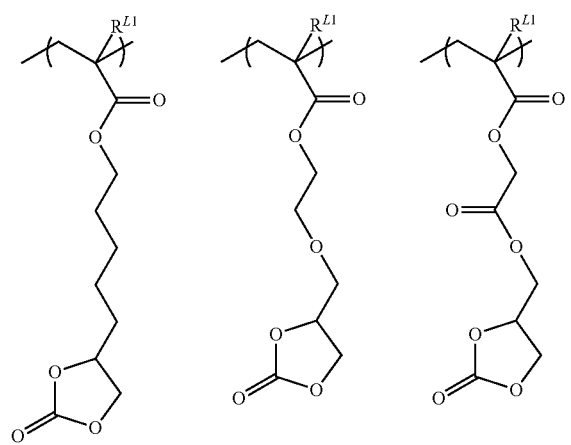
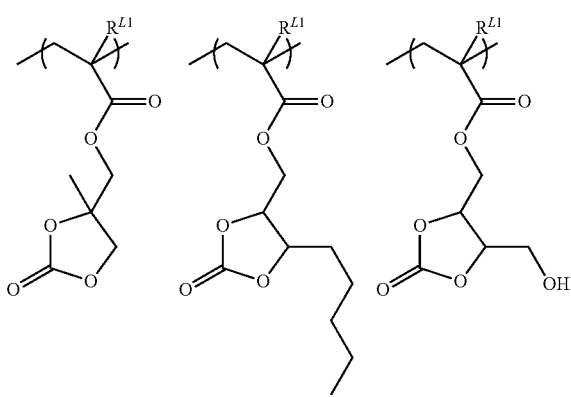
-continued
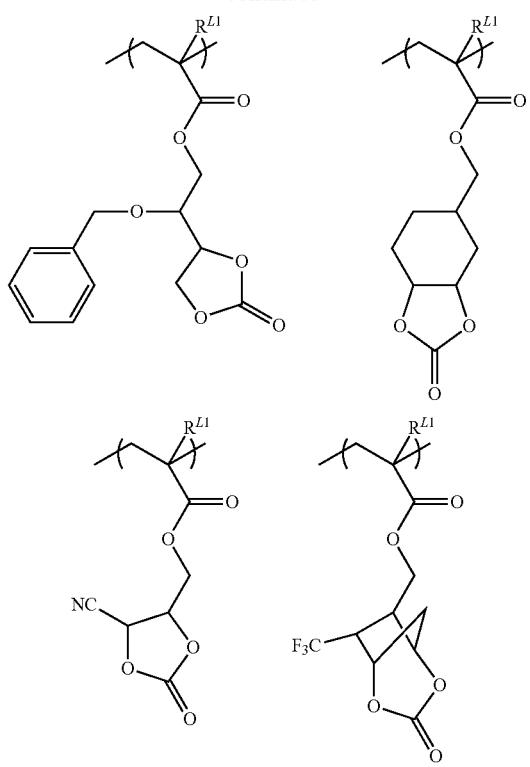
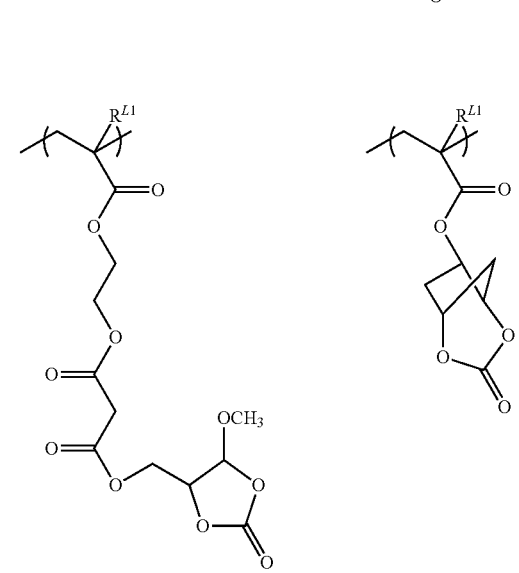
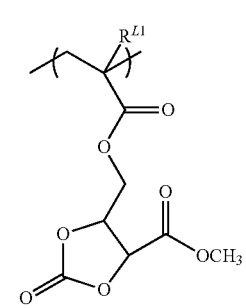
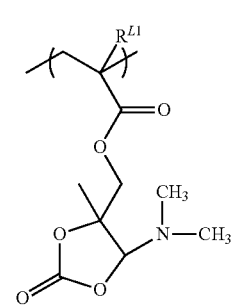

-continued

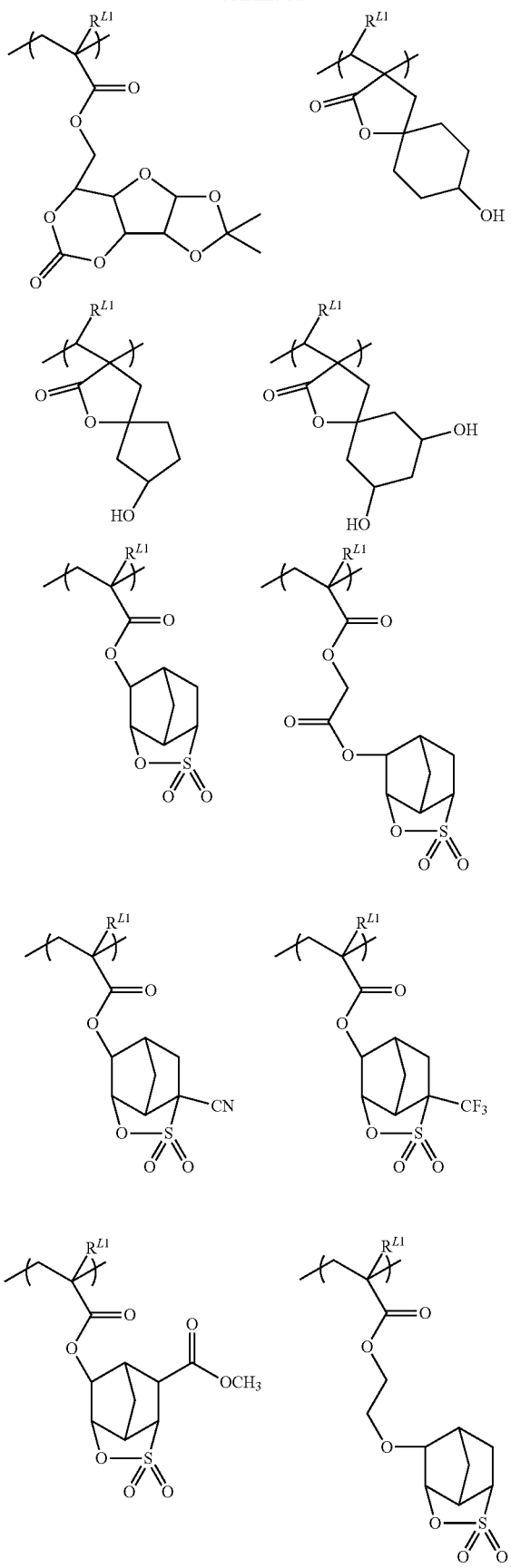

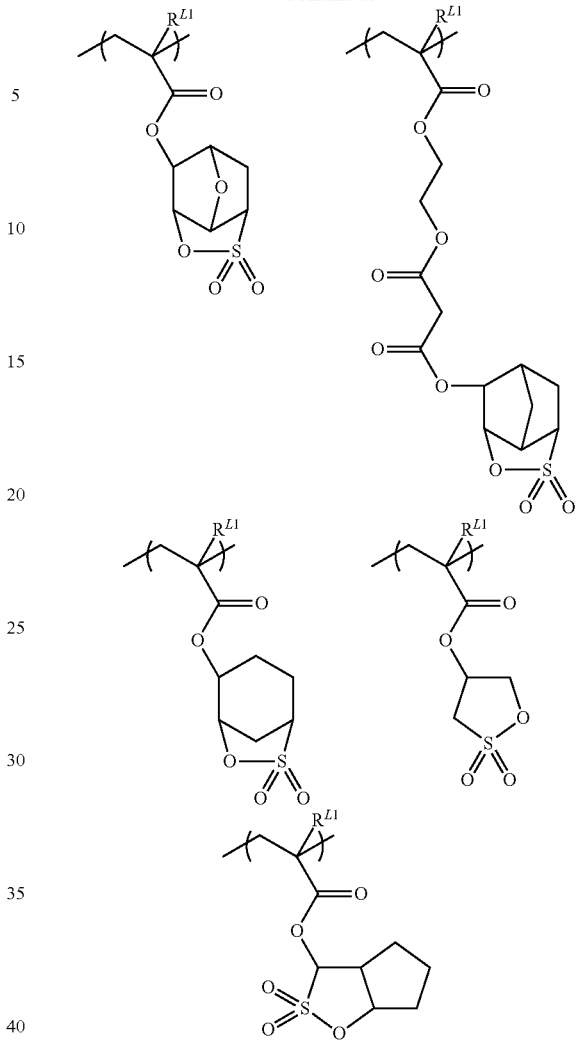

In the above formulae, $R^{L1}$ represents a hydrogen atom, a fluorine atom, a methyl group or a trifluoromethyl group.

Among these, as the structural unit (II), a structural unit that includes a lactone structure and a structural unit that includes a sultone structure are preferred, and a structural unit that includes a norbornanelactone structure and a structural unit that includes a norbornanesultone structure are more preferred.

The proportion of the structural unit (II) with respect to the total structural units constituting the polymer (A) is preferably 30 mol % to 80 mol %, more preferably 35 mol % to 70 mol %, and still more preferably 40 mol % to 60 mol %. When the proportion of the structural unit (II) is less than the lower limit, the adhesiveness of a resist pattern formed from the photoresist composition to a substrate may be deteriorated. On the other hand, when the proportion of the structural unit (II) is greater than the upper limit, the pattern formability of the photoresist composition may be deteriorated.

Other Structural Unit

The polymer (A) may include other structural unit that is different from the structural units (I) and (II). The other structural unit is exemplified by a first other structural unit that includes a polar group, and the like (except for those corresponding to the structural unit (I) and the structural unit (II)). Examples of the polar group include a hydroxy group, a carboxy group, a cyano group, a nitro group, a sulfonamide group, and the like. Among these, a hydroxy group and a carboxy group are preferred, and a hydroxy group is more preferred.

Examples of the structural unit that includes a polar group include structural units represented by the following formulae, and the like.

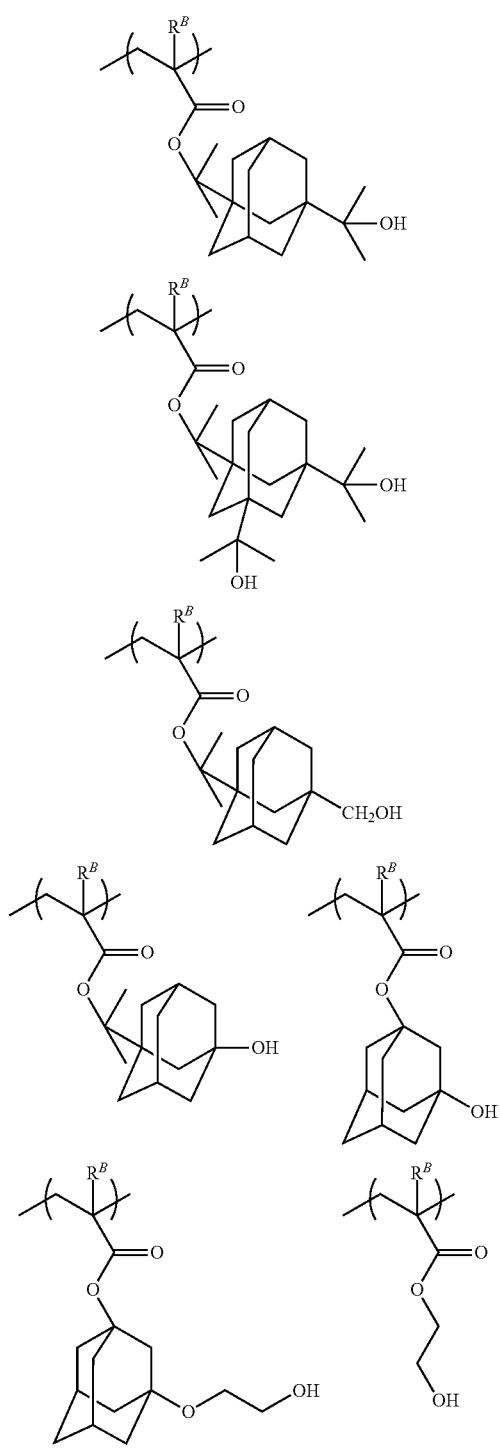

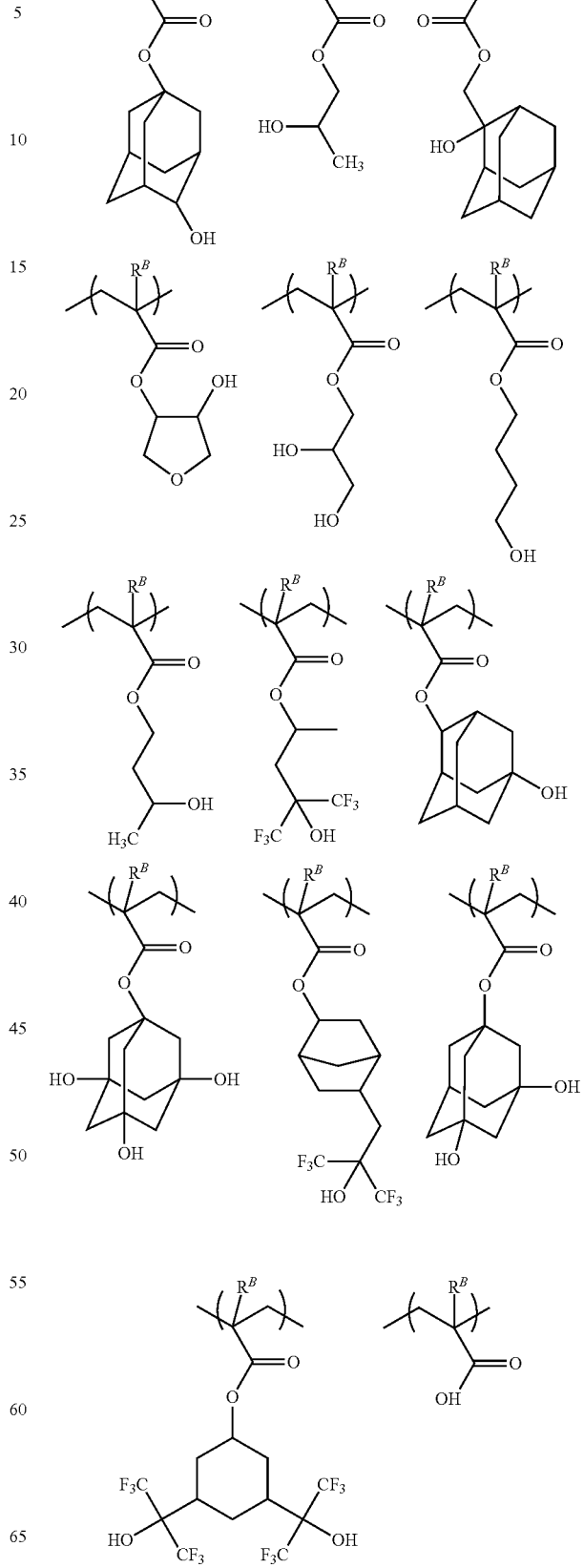

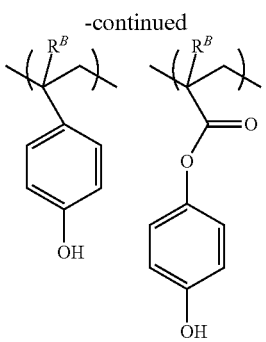

In the above formulae, $R^B$ represents a hydrogen atom, a fluorine atom, a methyl group or a trifluoromethyl group.

The proportion of the structural unit that includes a polar group with respect to the total structural units constituting the polymer (A) is preferably 0 mol % to 80 mol %, more preferably 0 mol % to 75 mol %, and still more preferably 30 mol % to 70 mol %. When the proportion of the structural unit that includes a polar group is greater than the upper limit, the pattern formability of the photoresist composition may be deteriorated.

The polymer (A) may include a second other structural unit as well as the first structural unit that includes a polar group. The proportion of the second other structural unit with respect to the total structural units constituting the polymer (A) is typically no greater than 30 mol %, and preferably no greater than 20 mol %. When the proportion of the second other structural unit is greater than the upper limit, the pattern formability of the photoresist composition may be deteriorated.

The content of the polymer (A) with respect to the total solid content of the photoresist composition is typically no less than 70% by mass, preferably no less than 80% by mass, and more preferably no less than 85% by mass.

Synthesis Method of Polymer (A)

The polymer (A) can be synthesized, for example, by polymerizing monomer(s) that give(s) each structural unit in an appropriate solvent using a radical polymerization initiator.

Examples of the radical polymerization initiator include azo radical initiators such as azobisisobutyronitrile (AIBN), 2,2'-azobis(4-methoxy-2,4-dimethylvaleronitrile), 2,2'-azobis(2-cyclopropylpropionitrile), 2,2'-azobis(2,4-dimethylvaleronitrile) and dimethyl 2,2'-azobisisobutyrate; peroxide radical initiators such as benzoyl peroxide, t-butyl hydroperoxide and cumene hydroperoxide; and the like. Among these, AIBN, dimethyl 2,2'-azobisisobutyrate are preferred, and AIBN are more preferred. These radical initiators may be used either alone, or as a mixture of two or more types thereof.

Examples of the solvent used in the polymerization include:

alkanes such as n-pentane, n-hexane, n-heptane, n-octane, n-nonane and n-decane;

cycloalkanes such as cyclohexane, cycloheptane, cyclooctane, decalin and norbornane;

aromatic hydrocarbons such as benzene, toluene, xylene, ethylbenzene and cumene;

halogenated hydrocarbons such as chlorobutanes, bromohexanes, dichloroethanes, hexamethylene dibromide and chlorobenzene;

saturated carboxylic acid esters such as ethyl acetate, n-butyl acetate, i-butyl acetate and methyl propionate;

ketones such as acetone, methyl ethyl ketone, 4-methyl-2-pentanone and 2-heptanone;

ethers such as tetrahydrofuran, diethoxyethanes and diethoxyethanes;

alcohols such as methanol, ethanol, 1-propanol, 2-propanol and 4-methyl-2-pentanol; and the like. These solvents used in the polymerization may be used either alone, or in combination of two or more types thereof.

The reaction temperature in the polymerization is typically 40° C. to 150° C., and preferably 50° C. to 120° C. The reaction time period is typically 1 hour to 48 hrs, and preferably 1 hour to 24 hrs.

Although the polystyrene equivalent weight average molecular weight (Mw) of the polymer (A) as determined by gel permeation chromatography (GPC) is not particularly limited, the Mw is preferably no less than 1,000 and no greater than 50,000, more preferably no less than 2,000 and no greater than 30,000, still more preferably no less than 3,000 and no greater than 20,000, and particularly preferably no less than 5,000 and no greater than 15,000. When the Mw of the polymer (A) is less than the lower limit, the heat resistance of the resulting resist film may be deteriorated. When the Mw of the polymer (A) is greater than the upper limit, the developability of the resist film may be deteriorated.

The ratio (Mw/Mn) of the Mw to the polystyrene equivalent number average molecular weight (Mn) as determined by GPC of the polymer (A) is typically no less than 1 and no greater than 5, preferably no less than 1 and no greater than 3, and still more preferably no less than 1 and no greater than 2.

The Mw and Mn of the polymer as used herein are determined using gel permeation chromatography (GPC) under the following conditions:

GPC columns: G2000HXL×2, G3000HXL×1, and G4000HXL×1 (each manufactured by Tosoh Corporation)

column temperature: 40° C.

elution solvent: tetrahydrofuran (manufactured by Wako Pure Chemical Industries, Ltd.)

flow rate: 1.0 mL/min sample concentration: 1.0% by mass amount of injected sample: 100 μL detector: differential refractometer standard substance: mono-dispersed polystyrene.

The content of low molecular weight components (the low molecular weight components mean components having a molecular weight of less than 1,000) in the polymer (A) is preferably no greater than 0.5% by mass, more preferably no greater than 0.2% by mass, and still more preferably no greater than 0.1% by mass. When the content of the low molecular weight components in the polymer (A) falls within the above range, the photoresist composition may lead to a further improvement of the rectangularity of a cross-sectional shape, the LWR performance, the resolving ability and the depth of focus.

The content of the low molecular weight components of the polymer as used herein is determined by high performance liquid chromatography (HPLC) using an Intersil ODS-25 μm column (4.6 mmφ×250 mm; manufactured by GL Sciences, Inc.) under the following conditions:

elution solvent: acrylonitrile/0.1% by mass aqueous phosphoric acid solution flow rate: 1.0 mL/min sample concentration: 1.0% by mass amount of injected sample: 100 μL detector: differential refractometer.

(B) Acid Generator

The acid generator (B) generates an acid upon an exposure. The acid-labile group included in the polymer (A) is dissociated by the acid to generate a polar group such as a carboxy group, whereby the solubility of the polymer (A) in a developer solution is altered. The mode of incorporation of the acid generator (B) in the photoresist composition may be in a low molecular weight compound form (hereinafter, may be also referred to as "(B) acid generating agent" or "acid generating agent (B)", as appropriate), as described later, or in a form of an acid generating group incorporated into the polymer as a part thereof, or in both of these forms.

The acid generating agent (B) is exemplified by an onium salt compound, an N-sulfonyloxyimide compound, a halogen-containing compound, a diazoketone compound, and the like.

The onium salt compound is exemplified by a sulfonium salt, a tetrahydrothiophenium salt, an iodonium salt, a phosphonium salt, a diazonium salt, a pyridinium salt, and the like.

Examples of the sulfonium salt include triphenylsulfonium trifluoromethanesulfonate, triphenylsulfonium nonafluoro-n-butanesulfonate, triphenylsulfonium perfluoro-n-octanesulfonate, triphenylsulfonium 2-bicyclo[2.2.1]hept-2-yl-1,1,2,2-tetrafluoroethanesulfonate, triphenylsulfonium 2-bicyclo[2.2.1]hept-2-yl-1,1-difluoroethanesulfonate, triphenylsulfonium camphorsulfonate, 4-cyclohexylphenyldiphenylsulfonium trifluoromethanesulfonate, 4-cyclohexylphenyldiphenylsulfonium nonafluoro-n-butanesulfonate, 4-cyclohexylphenyldiphenylsulfonium perfluoro-n-octanesulfonate, 4-cyclohexylphenyldiphenylsulfonium 2-bicyclo[2.2.1]hept-2-yl-1,1,2,2-tetrafluoroethanesulfonate, 4-cyclohexylphenyldiphenylsulfonium camphorsulfonate, 4-methanesulfonylphenyldiphenylsulfonium trifluoromethanesulfonate, 4-methanesulfonylphenyldiphenylsulfonium nonafluoro-n-butanesulfonate, 4-methanesulfonylphenyldiphenylsulfonium perfluoro-n-octanesulfonate, 4-methanesulfonylphenyldiphenylsulfonium 2-bicyclo[2.2.1]hept-2-yl-1,1,2,2-tetrafluoroethanesulfonate, 4-methanesulfonylphenyldiphenylsulfonium camphorsulfonate, triphenylsulfonium 1,1,2,2-tetrafluoro-6-(1-adamantanecarbonyloxy)-hexane-1-sulfonate, and the like.

Examples of the tetrahydrothiophenium salt include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium perfluoro-n-octanesulfonate, 1-(4-n-butoxynaphthalen-1-yl)tetrahydrothiophenium 2-bicyclo[2.2.1]hept-2-yl-1,1,2,2-tetrafluoroethanesulfonate, 1-(4-n-butoxynaphthalen-1-yl)tetrahydrothiophenium camphorsulfonate, 1-(6-n-butoxynaphthalen-2-yl)tetrahydrothiophenium trifluoromethanesulfonate, 1-(6-n-butoxynaphthalen-2-yl)tetrahydrothiophenium nonafluoro-n-butanesulfonate, 1-(6-n-butoxynaphthalen-2-yl)tetrahydrothiophenium perfluoro-n-octanesulfonate, 1-(6-n-butoxynaphthalen-2-yl)tetrahydrothiophenium 2-bicyclo[2.2.1]hept-2-yl-1,1,2,2-tetrafluoroethanesulfonate, 1-(6-n-butoxynaphthalen-2-yl)tetrahydrothiophenium camphorsulfonate, 1-(3,5-dimethyl-4-hydroxyphenyl)tetrahydrothiophenium trifluoromethanesulfonate, 1-(3,5-dimethyl-4-hydroxyphenyl)tetrahydrothiophenium nonafluoro-n-butanesulfonate, 1-(3,5-dimethyl-4-hydroxyphenyl)tetrahydrothiophenium perfluoro-n-octanesulfonate, 1-(3,5-dimethyl-4-hydroxyphenyl)tetrahydrothiophenium 2-bicyclo[2.2.1]hept-2-yl-1,2,2-tetrafluoroethanesulfonate, 1-(3,5-dimethyl-4-hydroxyphenyl)tetrahydrothiophenium camphorsulfonate, and the like.

Examples of the iodonium salt include diphenyliodonium trifluoromethanesulfonate, diphenyliodonium nonafluoro-n-butanesulfonate, diphenyliodonium perfluoro-n-octanesulfonate, diphenyliodonium 2-bicyclo[2.2.1]hept-2-yl-1,1,2,2-tetrafluoroethanesulfonate, diphenyliodonium camphorsulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, bis(4-t-butylphenyl)iodonium 2-bicyclo[2.2.1]hept-2-yl-1,1,2,2-tetrafluoroethanesulfonate, bis(4-t-butylphenyl)iodonium camphorsulfonate, and the like.

Examples of the N-sulfonyloxyimide compound include N-(trifluoromethanesulfonyloxy)bicyclo[2.2.1]hept-5-ene-2,3-dicarboxyimide, N-(nonafluoro-n-butanesulfonyloxy)bicyclo[2.2.1]hept-5-ene-2,3-dicarboxyimide, N-(perfluoro-n-octanesulfonyloxy)bicyclo[2.2.1]hept-5-ene-2,3-dicarboxyimide, N-(2-bicyclo[2.2.1]hept-2-yl-1,1,2,2-tetrafluoroethanesulfonyloxy)bicyclo[2.2.1]hept-5-ene-2,3-dicarboxyimide, N-(2-(3-tetracyclo[4.4.0.1$^{2,5}$.1$^{7,10}$]dodecanyl)-1,1-difluoroethanesulfonyloxy)bicyclo[2.2.1]hept-5-ene-2,3-dicarboxyimide, N-(camphorsulfonyloxy)bicyclo[2.2.1]hept-5-ene-2,3-dicarboxyimide, and the like.

Among these, as the acid generating agent (B), an onium salt compound is preferred, a sulfonium salt is more preferred, and triphenylsulfonium 2-bicyclo[2.2.1]hept-2-yl-1,1-difluoroethanesulfonate is still more preferred.

In a case where the acid generator (B) is the acid generating agent (B), the amount of the acid generator (B) with respect to 100 parts by mass of the polymer (A) is preferably no less than 0.1 parts by mass and no greater than 30 parts by mass, more preferably no less than 0.5 parts by mass and no greater than 20 parts by mass, and still more preferably no less than 1 part by mass and no greater than 15 parts by mass in light of attaining the sensitivity and developability of the photoresist composition. When the amount of the acid generating agent (B) falls within the above range, the sensitivity and developability of the photoresist composition may be improved. One, or two or more types of the acid generator (B) may be used.

(C) Acid Diffusion Control Agent

The acid diffusion control agent (C) contains the compound (1). When the photoresist composition contains the acid diffusion control agent (C) in addition to the polymer (A) and the acid generator (B), the photoresist composition leads to a superior rectangularity of a cross-sectional shape, a superior LWR performance, a superior resolving ability and a favorable depth of focus. One, or two or more types of the acid diffusion control agent (C) may be used.

Compound (1)

The compound (1) is represented by the above formula (1).

In the above formula (1), $R^1$, $R^2$ and $R^3$ each independently represent a hydrogen atom or a monovalent hydrocarbon group having 1 to 10 carbon atoms, wherein in a case where the monovalent hydrocarbon group is present in a plurality of number, at least two of these hydrocarbon groups optionally taken together represent a ring structure by binding with each other, together with the carbon atom to which the at least two of these hydrocarbon groups bond; A represents a group having a valency of n that is obtained by combining: at least one group selected from the group consisting of a hydrogen atom, a linear hydrocarbon group having 1 to 30 carbon atoms and an alicyclic hydrocarbon group having 3 to 30 carbon atoms; at least one group selected from the group consisting of —O—, —CO—, —COO—, —SO$_2$O—, —NR—, —NRSO$_2$—, —NRSO$_2$O— and —NRCO—; and n nitrogen atoms as a binding site to the carbonyl group in the above formula (1), wherein a sum of atomic masses of the atoms constituting A is no less than 120, wherein a part or all of hydrogen atoms included in the linear hydrocarbon group and the alicyclic hydrocarbon group are unsubstituted or substituted with a fluorine atom-free group, and wherein R represents a hydrogen atom or a monovalent hydrocarbon group having 1 to 10 carbon atoms; and n is an integer of 1 to 4.

The monovalent hydrocarbon group having 1 to 10 carbon atoms which may be represented by $R^1$, $R^2$ or $R^3$ is exemplified by a monovalent linear hydrocarbon group having 1 to 10 carbon atoms, a monovalent alicyclic hydrocarbon group having 3 to 10 carbon atoms, a monovalent aromatic hydrocarbon group having 6 to 10 carbon atoms, and the like.

Examples of the monovalent linear hydrocarbon group having 1 to 10 carbon atoms include:

alkyl groups such as a methyl group, an ethyl group, a n-propyl group, an i-propyl group, a n-butyl group, an i-butyl group, a sec-butyl group and a t-butyl group;

alkenyl groups such as an ethenyl group, a propenyl group and a butenyl group;

alkynyl groups such as an ethynyl group, a propynyl group and a butynyl group; and the like.

Examples of the monovalent alicyclic hydrocarbon group having 3 to 10 carbon atoms include:

monocyclic cycloalkyl groups such as a cyclopropyl group, a cyclobutyl group, a cyclopentyl group, a cyclohexyl group, a cycloheptyl group, a cyclooctyl group and a cyclodecyl group;

polycyclic cycloalkyl groups such as a norbornyl group, an adamantyl group and a tricyclodecyl group;

monocyclic cycloalkenyl groups such as a cyclopentenyl group and a cyclohexenyl group;

polycyclic cycloalkenyl groups such as a norbornenyl group and a tricyclodecenyl group; and the like.

Examples of the monovalent aromatic hydrocarbon group having 6 to 10 carbon atoms include:

aryl groups such as a phenyl group, a tolyl group, a xylyl group, a mesityl group and a naphthyl group;

aralkyl groups such as a benzyl group, a phenethyl group and a phenylpropyl group; and the like.

Examples of the ring structure which may be taken together represented by at least two of the hydrocarbon groups by binding with each other include:

monocyclic cycloalkane structures such as a cyclobutane structure, a cyclopentane structure, a cyclohexane structure, a cyclooctane structure and a cyclodecane structure and;

polycyclic cycloalkane structures such as a bicyclo[2.2.1] heptane structure, a bicyclo[2.2.2]octane structure, an adamantane structure and a tricyclodecane structure; and the like.

Among these, $R^1$, $R^2$ and $R^3$ represent preferably a hydrogen atom or a linear hydrocarbon group, more preferably a hydrogen atom or an alkyl group, still more preferably an alkyl group, and particularly preferably a methyl group or an ethyl group.

The group constituted with $R^1$, $R^2$, $R^3$ and the carbon atom to which $R^1$, $R^2$ and $R^3$ bond is preferably a t-butyl group or a t-amyl group.

Examples of the linear hydrocarbon group having 1 to 30 carbon atoms that constitutes A include groups obtained by eliminating at least one hydrogen atom from a linear hydrocarbon such as:

an alkane such as methane, ethane, propane, butane, isobutane, n-pentane, isopentane, n-hexane and isohexane;

an alkene such as ethene, propene, n-butene, isobutene, n-pentene and isopentene;

an alkyne such as ethyne, propyne, butyne and pentyne; and the like.

Examples of the alicyclic hydrocarbon group having 3 to 30 carbon atoms that constitutes A include groups obtained by eliminating at least one hydrogen atom from an alicyclic hydrocarbon such as:

a monocyclic cycloalkane such as cyclopropane, cyclobutane, cyclopentane, cyclohexane, cyclooctane and cyclodecane;

a polycyclic cycloalkane such as norbornane, adamantane and tricyclodecane;

a monocyclic cycloalkene such as cyclopropene, cyclobutene, cyclopentene, cyclohexene, cyclooctene and cyclodecene;

a polycyclic cycloalkene such as norbornene and tricyclodecene; and the like.

Examples of the fluorine atom-free substituent which may be included in the linear hydrocarbon group and the alicyclic hydrocarbon group include a cyano group, a nitro group, and the like.

Examples of the group that is obtained by combining: at least one group selected from the group consisting of a hydrogen atom, the linear hydrocarbon group and the alicyclic hydrocarbon group; and at least one group selected from the group consisting of —O—, —CO—, —COO—, —SO$_2$O—, —NR—, —NRSO$_2$—, —NRSO$_2$O— and —NRCO—, which constitute A, include cyclic ether groups, cyclic ketone groups, lactone groups, sultone groups, cyclic amino groups, cyclic sulfonamide groups, cyclic oxysulfonamide groups, lactam groups, alkoxy groups, acyl groups, acyloxy groups, alkylsulfonyloxy groups, alkoxysulfonyl groups, alkylamino groups, dialkylamino groups, alkoxyalkyl groups, acylalkyl groups, acyloxyalkyl groups, alkoxyalkyl groups, alkylsulfonyloxyalkyl groups, alkyliminosulfonyl groups, alkylsulfonylamidoalkyl groups, alkyliminosulfonyloxyalkyl groups, alkoxysulfonylamidoalkyl groups, alkyliminocarbonylalkyl groups, alkylcarbonyliminoalkyl groups, a hydroxy group, a formyl group, a carboxy group, a sulfo group, an amino group, and the like.

Examples of the monovalent hydrocarbon group having 1 to 10 carbon atoms which may be represented by R include groups similar to those exemplified as the monovalent hydrocarbon group having 1 to 10 carbon atoms in connection with $R^1$, $R^2$ and $R^3$, as described above, and the like.

Preferably, n is an integer of 1 to 3, more preferably 1 or 2, and still more preferably 1 in light of the ease in synthesis of the compound (1).

The lower limit of the sum of the atomic masses of the atoms constituting A is 120, preferably 150, more preferably 200, still more preferably 250, and particularly preferably 290. When the sum of the atomic masses of the atoms constituting A is less than the lower limit, the volatility of the compound generated from the compound (1) after the exposure tends to be elevated, and as a result, the photoresist composition may lead to deterioration of the rectangularity of a cross-sectional shape.

The upper limit of the sum of the atomic masses of the atoms constituting A is preferably 1,000, more preferably 800, still more preferably 600, and particularly preferably 500. When the sum of the atomic masses of the atoms constituting A is greater than the upper limit, the dispersibility of the compound (1) in the resist film may be reduced, resulting in the tendency that the rectangularity of a cross-sectional shape, the LWR performance, the resolving ability and the depth of focus of the photoresist composition are deteriorated.

The compound (1) is exemplified by compounds represented by the following formulae (i1) to (i21) (hereinafter, may be also referred to as "compounds (i1) to (i-21)"), and the like.

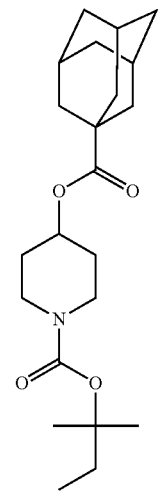

(i1)

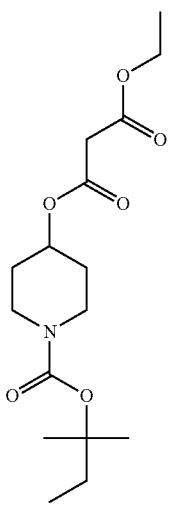

(i2)

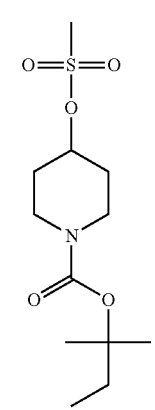

(i3)

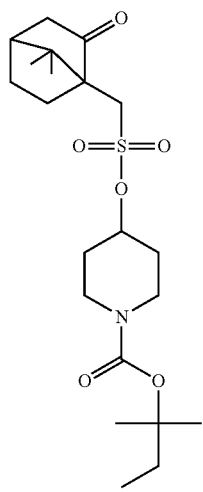

(i4)

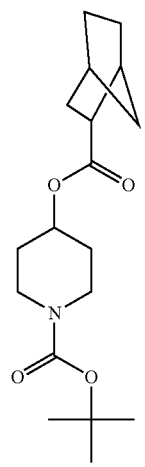

(i5)

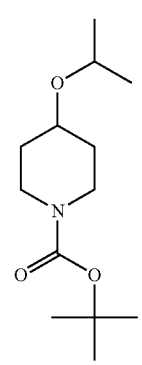

(i6)

-continued
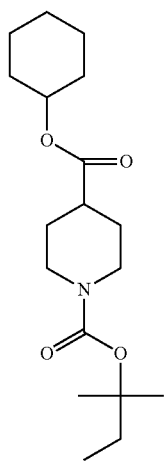
(i7)
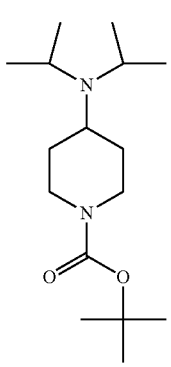
(i8)
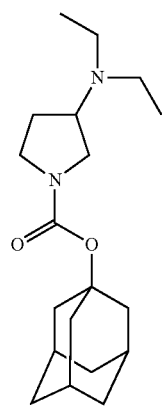
(i9)
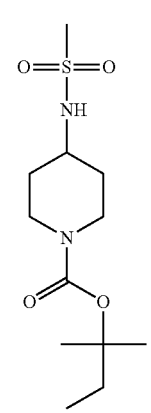
(i10)
-continued
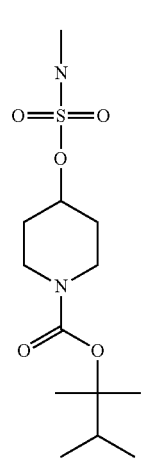
(i11)
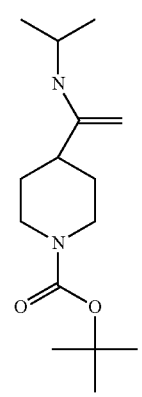
(i12)
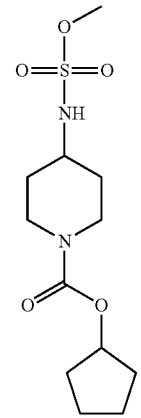
(i13)

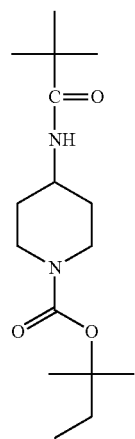
(i14)
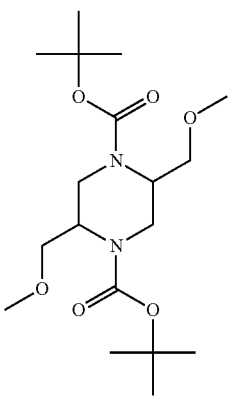
(i18)
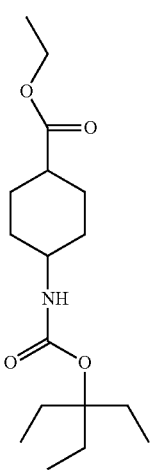
(i15)
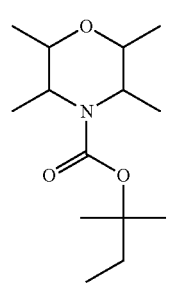
(i19)
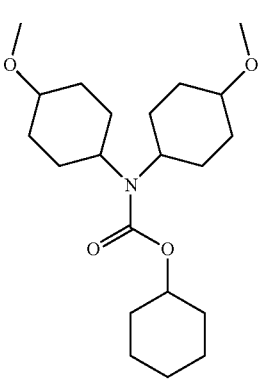
(i16)
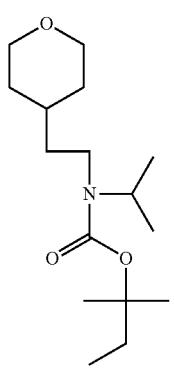
(i20)
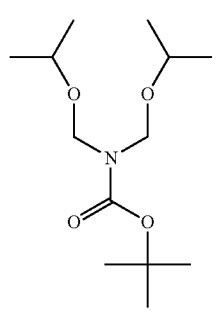
(i17)

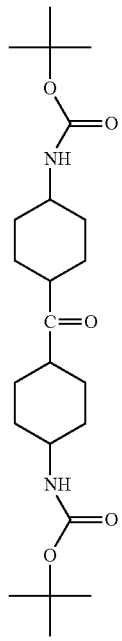

(i21)

The compound (1) is preferably the compound represented by the above formula (2) (hereinafter, may be also referred to as "compound (2)").

In the above formula (2), $R^1$, $R^2$, $R^3$ and n are as defined in the above formula (1); $R^4$ represents a hydrogen atom or a monovalent hydrocarbon group having 1 to 10 carbon atoms; $R^5$ represents a divalent hydrocarbon group having 1 to 10 carbon atoms, wherein $R^4$ and $R^5$ optionally taken together represent an alicyclic structure by binding with each other, together with the nitrogen atom to which $R^4$ and $R^5$ bond; $R^6$ represents a group having a valency of n that is obtained by combining: at least one group selected from the group consisting of a hydrogen atom, a linear hydrocarbon group having 1 to 30 carbon atoms and an alicyclic hydrocarbon group having 3 to 30 carbon atoms; and at least one group selected from the group consisting of —O—, —CO—, —COO—, —SO$_2$O—, —NR—, —NRSO$_2$—, —NRSO$_2$O— and —NRCO—, wherein a part or all of hydrogen atoms included in the linear hydrocarbon group and the alicyclic hydrocarbon group are unsubstituted or substituted with a fluorine atom-free group, wherein R represents a hydrogen atom or a monovalent hydrocarbon group having 1 to 10 carbon atoms, and wherein in the formula (2), a value obtained by the formula of: {[(a formula mass of $R^4$)+(a formula mass of $R^5$)+(an atomic mass of nitrogen)]×n+(a formula mass of $R^6$)} is no less than 120.

Examples of the monovalent hydrocarbon group having 1 to 10 carbon atoms which may be represented by $R^4$ include groups similar to those exemplified as the monovalent hydrocarbon group in connection with $R^1$, $R^2$ and $R^3$, as described above.

Examples of the divalent hydrocarbon group having 1 to 10 carbon atoms represented by $R^5$ include groups derived by eliminating one hydrogen atom from a group exemplified as the monovalent hydrocarbon group in connection with $R^1$, $R^2$ and $R^3$, as described above, and the like.

Examples of the ring structure which may be represented by $R^4$ and $R^5$ by binding with each other, together with the nitrogen atom to which $R^4$ and $R^5$ bond include:

monocyclic azacycloalkane structures such as an azacyclopropane structure, an azacyclobutane structure, an azacyclopentane structure (pyrrolidine structure), an azacyclohexane structure (piperidine structure), an azacycloheptane structure, an azacyclooctane structure and an azacyclodecane structure;

polycyclic azacycloalkane structures such as an azabicyclo[2.2.1]heptane structure, an azabicyclo[2.2.2]octane structure, an azatricyclo[3.3.1.1$^{3,7}$]decane structure; and the like.

Among these, monocyclic azacycloalkane structures are preferred, an azacyclopentane structure and an azacyclohexane structure are more preferred, and an azacyclohexane structure is still more preferred.

Examples of the linear hydrocarbon group having 1 to 30 carbon atoms that constitutes $R^6$ include groups similar to those exemplified as the linear hydrocarbon group in connection with the groups that constitute A, and the like.

Examples of the alicyclic hydrocarbon group having 3 to 30 carbon atoms that constitutes $R^6$ include groups similar to those exemplified as the alicyclic hydrocarbon group in connection with the groups that constitute A, and the like.

Examples of the group, which is represented by $R^6$, having a valency of n that is obtained by combining: at least one selected from the group consisting of a hydrogen atom, a linear hydrocarbon group and an alicyclic hydrocarbon group; and at least one group selected from the group consisting of —O—, —CO—, —COO—, —SO$_2$O—, —NR—, —NRSO$_2$—, —NRSO$_2$O— and —NRCO— include cyclic ether groups, cyclic ketone groups, lactone groups, sultone groups, cyclic amino groups, cyclic sulfonamide groups, cyclic oxysulfonamide groups, lactam groups, alkoxy groups, acyl groups, acyloxy groups, alkylsulfonyloxy groups, alkoxysulfonyl groups, alkylamino groups, dialkylamino groups, alkoxyalkyl groups, acylalkyl groups, acyloxyalkyl groups, alkoxyalkyl groups, alkylsulfonyloxyalkyl groups, alkyliminosulfonyl groups, alkylsulfonylamidoalkyl groups, alkyliminosulfonyloxyalkyl groups, alkoxysulfonylamidoalkyl groups, alkyliminocarbonylalkyl groups, alkylcarbonyliminoalkyl groups, a hydroxy group, a formyl group, a carboxy group, a sulfo group, an amino group, and the like.

Examples of the fluorine atom-free substituent that may be included in $R^6$ include a cyano group, a nitro group, and the like.

The lower limit of the value obtained by the formula of: [(a formula mass of $R^4$+a formula mass of $R^5$+an atomic mass of nitrogen)×n+(a formula mass of $R^6$)] (hereinafter, may be also referred to as "the total atomic mass (1)") in the above formula (2) is 120, preferably 150, more preferably 200, still more preferably 250, and particularly preferably 290. When the total atomic mass (1) is less than the lower limit, the volatility of the compound generated from the compound (2) after the exposure may be elevated, resulting in the tendency that the rectangularity of a cross-sectional shape of the photoresist composition is deteriorated.

The upper limit of the total atomic mass (1) is preferably 1,000, more preferably 800, still more preferably 600, and particularly preferably 500. When the total atomic mass (1) is greater than the upper limit, the dispersibility of the compound (2) in the resist film may be reduced, resulting in the tendency that the photoresist composition leads to deterioration of the rectangularity of a cross-sectional shape, the LWR performance, the resolving ability and the depth of focus. It is to be noted that the formula mass of the group as referred to means a sum of atomic masses of the atoms constituting the group.

The compound (2) is exemplified by the compounds (i1) to (i15), (i19), and (i20), and the like.

The compound (2) is preferably the compound (i). The compound (i) is represented by the above formula (3).

In the above formula (3), $R^1$ to $R^5$ are as defined in the above formula (2); $R^7$, $R^8$ and $R^9$ each independently represent at least one group selected from the group consisting of a hydrogen atom, a linear hydrocarbon group having 1 to 30 carbon atoms and an alicyclic hydrocarbon group having 3 to 30 carbon atoms, or a group that is obtained by combining: the at least one group selected from the group consisting of a hydrogen atom, a linear hydrocarbon group having 1 to 30 carbon atoms and an alicyclic hydrocarbon group having 3 to 30 carbon atoms; and the at least one group selected from the group consisting of —O—, —CO—, —COO—, —SO$_2$O—, —NR—, —NRSO$_2$—, —NRSO$_2$O— and —NRCO—, wherein at least two of $R^7$, $R^8$ and $R^9$ optionally taken together represent a ring structure by binding with each other, together with the carbon atom to which the at least two of $R^7$, $R^8$ and $R^9$ bond; and X represents —O—, —CO—, —COO—, —SO$_2$O—, —NR—, —NRSO$_2$—, —NRSO$_2$O— or —NRCO—, and wherein a sum of formula masses of $R^4$, $R^5$, X, $R^7$, $R^8$ and $R^9$ and atomic masses of the nitrogen and the carbon in the formula (3) is no less than 120.

Examples of the linear hydrocarbon group having 1 to 30 carbon atoms and the alicyclic hydrocarbon group having 3 to 30 carbon atoms which may be represented by $R^7$, $R^8$ or $R^9$ include groups similar to those exemplified as the linear hydrocarbon group and the alicyclic hydrocarbon group in connection with A in the above formula (1), and the like.

Examples of the group that is obtained by combining: the at least one group selected from the group consisting of a hydrogen atom, a linear hydrocarbon group having 1 to 30 carbon atoms and an alicyclic hydrocarbon group having 3 to 30 carbon atoms; and the at least one group selected from the group consisting of —O—, —CO—, —COO—, —SO$_2$O—, —NR—, —NRSO$_2$—, —NRSO$_2$O— and —NRCO— include cyclic ether groups, cyclic ketone groups, lactone groups, sultone groups, cyclic amino groups, cyclic sulfonamide groups, cyclic oxysulfonamide groups, lactam groups, alkoxy groups, acyl groups, acyloxy groups, alkylsulfonyloxy groups, alkoxysulfonyl groups, alkylamino groups, dialkylamino groups, alkoxyalkyl groups, acylalkyl groups, acyloxyalkyl groups, alkoxyalkyl groups, alkylsulfonyloxyalkyl groups, alkyliminosulfonyl groups, alkylsulfonylamidoalkyl groups, alkyliminosulfonyloxyalkyl groups, alkoxysulfonylamidoalkyl groups, alkyliminocarbonylalkyl groups, alkylcarbonyliminoalkyl groups, a hydroxy group, a formyl group, a carboxy group, a sulfo group, an amino group, and the like.

$R^7$, $R^8$ and $R^9$ represent preferably a hydrogen atom, a linear hydrocarbon group or an alkoxycarbonylalkyl group, more preferably a hydrogen atom, a methyl group or an ethoxycarbonyl group, and still more preferably a hydrogen atom or an ethoxycarbonyl group.

Examples of the ring structure taken together represented by at least two of $R^7$, $R^8$ and $R^9$ by binding with each other, together with the carbon atom to which the at least two of $R^7$, $R^8$ and $R^9$ bond include:

monocyclic alicyclic structures such as a cyclopentane structure and a cyclohexane structure;

polycyclic alicyclic structures such as a norbornane structure, an adamantane structure and a camphor structure; and the like.

Among these, polycyclic alicyclic structures are preferred, and an adamantane structure and a camphor structure are more preferred.

X represents preferably —O—, —COO— or —SO$_2$O—, more preferably —COO—, —SO$_2$O—, and still more preferably —COO—*, —SO$_2$O—* (* denotes a binding site to $R^5$ in the above formula (3)).

The lower limit of the sum of the formula masses of $R^4$, $R^5$, X, $R^7$, $R^8$ and $R^9$ and the atomic masses of the nitrogen and the carbon in the formula (3) (hereinafter, may be also referred to as "the total atomic mass (2)") is 120, preferably 150, more preferably 200, still more preferably 250, and particularly preferably 290. When the total atomic mass (2) is less than the lower limit, the volatility of the compound generated from the compound (i) after the exposure may be elevated, resulting in the tendency that the rectangularity of a cross-sectional shape of the photoresist composition is deteriorated.

The upper limit of the total atomic mass (2) is preferably 1,000, more preferably 800, still more preferably 600, and particularly preferably 500. When the total atomic mass (2) is greater than the upper limit, the dispersibility of the compound (i) in the resist film may be reduced, resulting in the tendency that the photoresist composition leads to deterioration of the rectangularity of a cross-sectional shape, the LWR performance, the resolving ability and the depth of focus.

Examples of the compound (i) include the compounds (i-1) to (i-15), and the like.

The compound (i) can be synthesized in accordance with the following reaction scheme, for example.

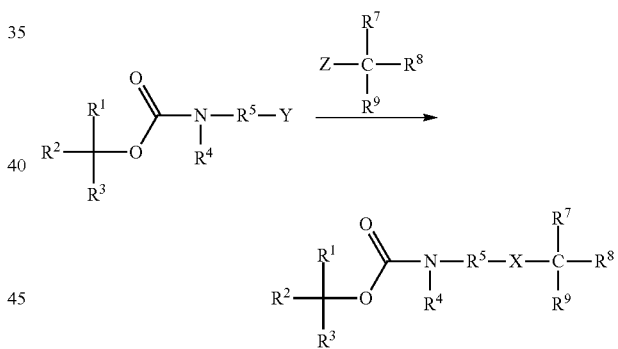

In the reaction scheme, $R^1$, $R^2$ and $R^3$ each independently represent a hydrogen atom or a monovalent hydrocarbon group having 1 to 10 carbon atoms, wherein in a case where the monovalent hydrocarbon group is present in a plurality of number, at least two of these hydrocarbon groups optionally taken together represent a ring structure by binding with each other, together with the carbon atom to which the at least two of these hydrocarbon groups bond; $R^4$ represents a hydrogen atom or a monovalent hydrocarbon group having 1 to 10 carbon atoms; $R^5$ represents a divalent hydrocarbon group having 1 to 10 carbon atoms, wherein $R^4$ and $R^5$ optionally taken together represent an alicyclic structure by binding with each other, together with the nitrogen atom to which $R^4$ and $R^5$ bond; $R^7$, $R^8$ and $R^9$ each independently represent at least one group selected from the group consisting of a hydrogen atom, a linear hydrocarbon group having 1 to 30 carbon atoms and an alicyclic hydrocarbon group having 3 to 30 carbon atoms, or a group that is obtained by combining: the at least one group selected from the group consisting of a hydrogen atom, a linear hydrocarbon group having 1 to 30 carbon atoms and an alicyclic hydrocarbon group having 3 to 30 carbon atoms; and the at least one group selected from the group consisting of —O—, —CO—, —COO—, —SO$_2$O—, —NR—, —NRSO$_2$—, —NRSO$_2$O— and —NRCO—, wherein at least two of R$^7$, R$^8$ and R$^9$ optionally taken together represent a ring structure by binding with each other, together with the carbon atom to which the at least two of R$^7$, R$^8$ and R$^9$ bond; and X represents —O—, —CO—, —COO—, —SO$_2$O—, —NR—, —NRSO$_2$—, —NRSO$_2$O— or —NRCO—; and Y and Z represent a group that forms X through a condensation reaction.

The combination of Y with Z and the resulting X are exemplified by the following, and the like:

when one of Y and Z represents a hydroxy group or a halogen atom and the rest of Y and Z represents a hydroxy group, —O— as X is obtained;

when one of Y and Z represents a hydroxy group and the rest of Y and Z represents a halocarbonyl group, a carboxy group or an acid anhydride group, —COO— as X is obtained;

when one of Y and Z represents a hydroxy group and the rest of Y and Z represents a halosulfonyl group or a sulfo group, —SO$_2$O— as X is obtained;

when one of Y and Z represents —NHR and the rest of Y and Z represents a halogen atom, —NR— as X is obtained;

when one of Y and Z represents —NHR and the rest of Y and Z represents a halosulfonyl group or a sulfo group, —NRSO$_2$— as X is obtained;

when one of Y and Z represents —NHR and the rest of Y and Z represents a halosulfonyloxy group or a sulfoxy group, —NRSO$_2$O— as X is obtained; and when one of Y and Z represents —NHR and the rest of Y and Z represents a halocarbonyl group, a carboxy group or an acid anhydride group, —NRCO— as X is obtained.

The compound (i) that includes X can be obtained, for example, by reacting the compound that includes Y with the compound that includes Z, in a solvent such as dichloromethane in the presence of a base such as triethylamine or dimethylaminopyridine (DMAP).

The content of the acid diffusion control agent (C) with respect to the acid generating agent (B) is preferably 1 mol % to 100 mol %, more preferably 3 mol % to 70 mol %, and still more preferably 5 mol % to 50 mol %, in light of the possibility that the photoresist composition leads to an improvement of the LWR performance, an EL (Exposure Latitude) performance and the rectangularity of a cross-sectional shape. When the content of the acid diffusion control agent (C) falls within the above range, the photoresist composition may lead to an improvement of the rectangularity of a cross-sectional shape, the LWR performance, the resolving ability and the sensitivity.

Moreover, the amount of the acid diffusion control agent (C) with respect to 100 parts by mass of the polymer (A) is preferably no less than 0.1 parts by mass and no greater than 30 parts by mass, more preferably no less than 0.5 parts by mass and no greater than 20 parts by mass, and still more preferably no less than 1 part by mass and no greater than 15 parts by mass.

Optional Component(s)
(D) Other Acid Diffusion Controller

The photoresist composition according to the embodiment of the present invention may contain (D) other acid diffusion controller, as needed. When the photoresist composition further contains the other acid diffusion controller (D) in addition to the acid diffusion control agent (C), the rectangularity of a cross-sectional shape, the LWR performance, the resolving ability and the depth of focus may be further improved. Although it is not necessarily clear why the aforementioned effect may be further improved when the other acid diffusion controller (D) is further contained, it may be presumed, for example, that a degree of diffusion of the compound as a whole contained in the acid diffusion control agent can be adjusted; and the like. The mode of incorporation of the other acid diffusion controller (D) in the photoresist composition may be in an acid diffusion control agent form which is a low molecular weight compound (hereinafter, may be also referred to as "(D) other acid diffusion control agent" or "other acid diffusion control agent (D)", as appropriate), as described later, or in a form of an acid diffusion control group incorporated into the polymer as a part thereof, or in both of these forms.

The other acid diffusion control agent (D) is exemplified by a compound represented by the following formula (5) (hereinafter, may be also referred to as "nitrogen-containing compound (I)"), a compound including two nitrogen atoms in a single molecule (hereinafter, may be also referred to as "nitrogen-containing compound (II)"), a compound including three nitrogen atoms (hereinafter, may be also referred to as "nitrogen-containing compound (III)"), an amide group-containing compound, a urea compound, a nitrogen-containing heterocyclic compound, and the like.

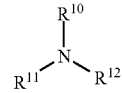

(5)

In the above formula (5), R$^{10}$, R$^{11}$ and R$^{12}$ each independently represent a hydrogen atom, a linear, branched or cyclic alkyl group, an aryl group or an aralkyl group each unsubstituted or substituted.

Examples of the nitrogen-containing compound (I) include monoalkylamines such as n-hexylamine; dialkylamines such as di-n-butylamine; trialkylamines such as triethylamine; aromatic amines such as aniline; and the like.

Examples of the nitrogen-containing compound (II) include ethylenediamine, N,N,N',N'-tetramethylethylenediamine, and the like.

Examples of the nitrogen-containing compound (III) include polyamine compounds such as polyethyleneimine and polyallylamine; polymers of dimethylaminoethylacrylamide, etc.; and the like.

Examples of the amide group-containing compound include formamide, N-methylformamide, N,N-dimethylformamide, acetamide, N-methylacetamide, N,N-dimethylacetamide, propionamide, benzamide, pyrrolidone, N-methylpyrrolidone, and the like.

Examples of the urea compound include urea, methylurea, 1,1-dimethylurea, 1,3-dimethylurea, 1,1,3,3-tetramethylurea, 1,3-diphenylurea, tributylthiourea, and the like.

Examples of the nitrogen-containing heterocyclic compound include pyridines such as pyridine and 2-methylpyridine, pyrazine, pyrazole, and the like.

A compound that includes an acid-labile group may also be used as the nitrogen-containing organic compound. Examples of such a nitrogen-containing organic compound that includes an acid-labile group include N-(t-butoxycarbonyl)piperidine, N-(t-butoxycarbonyl)imidazole, N-(t-butoxycarbonyl)benzimidazole, N-(t-butoxycarbonyl)-2-phenylbenzimidazole, N-(t-butoxycarbonyl)di-n-octylamine, N-(t-butoxycarbonyl)-diethanolamine, N-(t-butoxycarbonyl)-dicyclohexylamine, N-(t-butoxycarbonyl)-diphenylamine, N-(t-butoxycarbonyl)-4-hydroxypiperidine, and the like.

Moreover, a photodegradable base that is sensitized upon an exposure to generate a weak acid may be used as the other acid diffusion controller (D). Examples of the photodegradable base include onium salt compounds that are degraded upon an exposure and lose its acid diffusion controlling ability, and the like. Examples of the onium salt compound include a sulfonium salt compound represented by the following formula (6-1), an iodonium salt compound represented by the following formula (6-2), and the like.

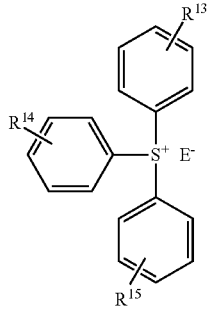

(6-1)

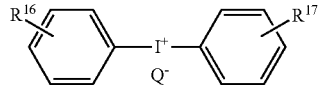

(6-2)

In the above formulae (6-1) and (6-2), $R^{13}$ to $R^{17}$ each independently represent a hydrogen atom, an alkyl group, an alkoxy group, a hydroxy group or a halogen atom; $E^-$ and $Q^-$ each independently represent $OH^-$, $R^\beta COO^-$, $R^\beta$—$SO_3^-$ or an anion represented by the following formula (6-3), wherein $R^\beta$ represents an alkyl group, an aryl group or an aralkyl group.

(6-3)

In the above formula (6-3), $R^{18}$ represents a linear or branched alkyl group having 1 to 12 carbon atoms, or a linear or branched alkoxyl group having 1 to 12 carbon atoms, wherein a part or all of hydrogen atoms included in the linear or branched alkyl group and the linear or branched alkoxyl group are unsubstituted or substituted with a fluorine atom; and u is an integer of 0 to 2.

In a case where the other acid diffusion controller (D) is the other acid diffusion control agent (D), the content of the other acid diffusion controller (D) with respect of the acid generating agent (B) is preferably 1 mol % to 100 mol %, more preferably 3 mol % to 70 mol %, and still more preferably 5 mol % to 50 mol %. When the content of the other acid diffusion control agent (D) is greater than the upper limit, the photoresist composition may lead to deterioration of the sensitivity, the rectangularity of a cross-sectional shape, the LWR performance, the resolving ability and the depth of focus.

Moreover, the amount of the other acid diffusion control agent (D) with respect to 100 parts by mass of the polymer (A) is preferably 0 to 20 parts by mass, more preferably 0.1 parts by mass to 15 parts by mass, and still more preferably 0.3 parts by mass to 10 parts by mass.

(E) Fluorine-Containing Polymer

The photoresist composition according to the embodiment of the present invention may contain (E) a fluorine-containing polymer (except for those corresponding to the polymer (A)). When the photoresist composition contains the fluorine-containing polymer (E), in forming a resist film, the fluorine-containing polymer (E) tends to be unevenly distributed in the vicinity of the surface of the resist film due to oil repellent characteristics of the fluorine-containing polymer in the film, and thus elution of the acid generating agent, the acid diffusion control agent and the like into a liquid immersion medium can be inhibited during an exposure through the liquid immersion medium. In addition, due to water repellent characteristics of the fluorine-containing polymer (E), an advancing contact angle of the liquid immersion medium on the resist film can be controlled to fall within a desired range, whereby formation of bubble defects can be inhibited. Furthermore, a larger receding contact angle of the liquid immersion medium on the resist film is attained, thereby enabling an exposure by high-speed scanning without being accompanied by residual water beads. Thus, when the photoresist composition contains the fluorine-containing polymer (E), a resist film suitable for a liquid immersion lithography process can be formed.

The fluorine-containing polymer (E) is not particularly limited as long as the fluorine-containing polymer (E) contains a fluorine atom; however, it is preferred that the fluorine-containing polymer (E) has a higher content (% by mass) of fluorine atoms than that of the polymer (A) in the photoresist composition. When the fluorine-containing polymer (E) has a higher content (% by mass) of fluorine atoms than that of the polymer (A), a higher degree of the aforementioned uneven distribution is attained, leading to an improvement of characteristics such as water repellency and elution inhibitory ability of the resulting resist film.

The content of fluorine atoms of the fluorine-containing polymer (E) falls within a range of preferably no less than 1% by mass, more preferably 2% by mass to 60% by mass, still more preferably 4% by mass to 40% by mass, and particularly preferably 7% by mass to 30% by mass. When the content of fluorine atoms of the fluorine-containing polymer (E) is less than the lower limit, the hydrophobicity of the surface of the resist film may be deteriorated. It is to be noted that the content (% by mass) of fluorine atoms of the polymer can be calculated based on the structure of the polymer as determined by $^{13}$C-NMR spectroscopy.

The fluorine-containing polymer (E) preferably has at least one selected from the group consisting of the following structural unit (Ea) and the following structural unit (Eb). The fluorine-containing polymer (E) may have one, or two or more types of the structural unit (Ea) and/or the structural unit (Eb).

Structural Unit (Ea)

The structural unit (Ea) is represented by the following formula (7a). When the fluorine-containing polymer (E) has the structural unit (Ea), the content of fluorine atoms thereof can be adjusted.

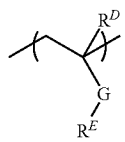

(7a)

In the above formula (7a), $R^D$ represents a hydrogen atom, a methyl group or a trifluoromethyl group; G represents a single bond, an oxygen atom, a sulfur atom, —CO—O—, —SO$_2$—O—NH—, —CO—NH— or —O—CO—NH—; $R^E$ represents a monovalent linear hydrocarbon group having 1 to 6 carbon atoms and having at least one fluorine atom, or a monovalent aliphatic cyclic hydrocarbon group having 4 to 20 carbon atoms and having at least one fluorine atom.

Examples of the linear hydrocarbon group having 1 to 6 carbon atoms and having at least one fluorine atom which may be represented by $R^E$ include a trifluoromethyl group, a 2,2,2-trifluoroethyl group, a perfluoroethyl group, a 2,2,3,3,3-pentafluoropropyl group, a 1,1,1,3,3,3-hexafluoropropyl group, a perfluoro-n-propyl group, a perfluoro-i-propyl group, a perfluoro-n-butyl group, a perfluoro-i-butyl group, a perfluoro-t-butyl group, a 2,2,3,3,4,4,5,5-octafluoropentyl group, a perfluorohexyl group, and the like.

Examples of the aliphatic cyclic hydrocarbon group having 4 to 20 carbon atoms and having at least one fluorine atom which may be represented by $R^E$ include a monofluorocyclopentyl group, a difluorocyclopentyl group, a perfluorocyclopentyl group, a monofluorocyclohexyl group, a difluorocyclopentyl group, a perfluorocyclohexylmethyl group, a fluoronorbornyl group, a fluoroadamantyl group, a fluorobornyl group, a fluoroisobornyl group, a fluorotricyclodecyl group, a fluorotetracyclodecyl group, and the like.

Examples of the monomer that gives the structural unit (Ea) include (meth)acrylic acid trifluoromethyl ester, (meth)acrylic acid 2,2,2-trifluoroethyl ester, (meth)acrylic acid perfluoroethyl ester, (meth)acrylic acid perfluoro-n-propyl ester, (meth)acrylic acid perfluoro-i-propyl ester, (meth)acrylic acid perfluoro-n-butyl ester, (meth)acrylic acid perfluoro-i-butyl ester, (meth)acrylic acid perfluoro-t-butyl ester, (meth)acrylic acid 2-(1,1,1,3,3,3-hexafluoropropyl) ester, (meth)acrylic acid 1-(2,2,3,3,4,4,5,5-octafluoropentyl) ester, (meth)acrylic acid perfluorocyclohexylmethyl ester, (meth)acrylic acid 1-(2,2,3,3,3-pentafluoropropyl) ester, (meth)acrylic acid monofluorocyclopentyl ester, (meth)acrylic acid difluorocyclopentyl ester, (meth)acrylic acid perfluorocyclopentyl ester, (meth)acrylic acid monofluorocyclohexyl ester, (meth)acrylic acid difluorocyclopentyl ester, (meth)acrylic acid perfluorocyclohexylmethyl ester, (meth)acrylic acid fluoronorbornyl ester, (meth)acrylic acid fluoroadamantyl ester, (meth)acrylic acid fluorobornyl ester, (meth)acrylic acid fluoroisobornyl ester, (meth)acrylic acid fluorotricyclodecyl ester, (meth)acrylic acid fluorotetracyclodecyl ester, and the like.

The proportion of structural unit (Ea) with respect to the total structural units constituting the fluorine-containing polymer (E) is preferably 5 mol % to 80 mol %, more preferably 10 mol % to 60 mol %, and still more preferably 15 mol % to 40 mol %. When the proportion of the structural unit (Ea) falls within the above range, a larger dynamic contact angle on the surface of the resist film may be attained in an exposure through a liquid immersion medium.

Structural Unit (Eb)

The structural unit (Eb) is represented by the following formula (7b). When the fluorine-containing polymer (E) has the structural unit (Eb), the hydrophobicity thereof may be enhanced, leading to a further improvement of the dynamic contact angle on the surface of the resist film formed from the photoresist composition.

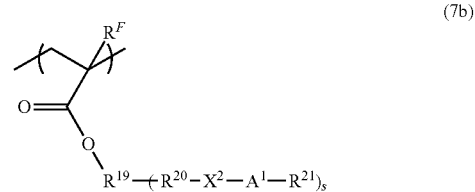

(7b)

In the above formula (7b), $R^F$ represents a hydrogen atom, a methyl group or a trifluoromethyl group; $R^{19}$ represents a hydrocarbon group having 1 to 20 carbon atoms and a valency of (s+1), which may further include an oxygen atom, a sulfur atom, —NR'—, a carbonyl group, —CO—O— or —CO—NH— at an end of $R^{19}$ on the $R^{20}$ side, wherein R' represents a hydrogen atom or a monovalent organic group; $R^{20}$ represents a single bond, a divalent linear hydrocarbon group having 1 to 10 carbon atoms or a divalent aliphatic cyclic hydrocarbon group having 4 to 20 carbon atoms; $X^2$ represents a divalent linear hydrocarbon group having 1 to 20 carbon atoms and having at least one fluorine atom; $A^1$ represents an oxygen atom, —NR"—, —CO—O—* or —SO$_2$—O—*, wherein R" represents a hydrogen atom or a monovalent organic group, and * denotes a binding site to $R^{19}$; $R^{21}$ represents a hydrogen atom or a monovalent organic group; and s is an integer of 1 to 3, wherein in a case where s is 2 or 3, a plurality of $R^{20}$s are identical to or different with each other, a plurality of $X^2$s are identical to or different with each other, a plurality of $A^1$s are identical to or different with each other, and a plurality of $R^{21}$s are identical to or different with each other.

$R^{21}$ preferably represents a hydrogen atom in light of the possibility of an increase of the solubility of the fluorine-containing polymer (E) in an alkaline developer solution.

Examples of the monovalent organic group which may be represented by $R^{21}$ include hydrocarbon groups having 1 to 30 carbon atoms and optionally including an acid-labile group, an alkali-labile group or a substituent, and the like.

Examples of the structural unit (Eb) include structural units represented by the following formulae (7b-1) to (7b-3), and the like.

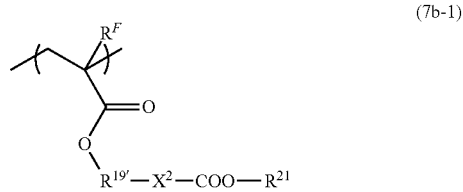

(7b-1)

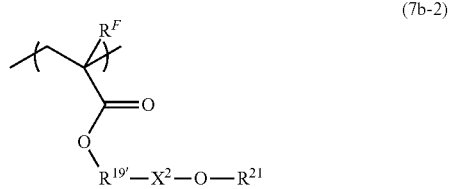

(7b-2)

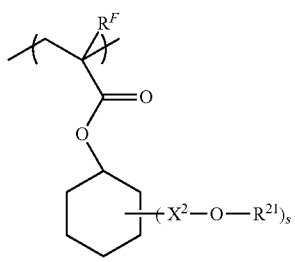
(7b-3)

In the above formulae (7b-1) to (7b-3), $R^{19'}$ represents a divalent linear, branched or cyclic saturated or unsaturated hydrocarbon group having 1 to 20 carbon atoms; and $R^F$, $X^2$, $R^{21}$ and s are as defined in the above formula (7b), wherein in a case where s is 2 or 3, a plurality of $X^2$s are identical to or different with each other, and a plurality of $R^{21}$s are identical to or different with each other.

The proportion of the structural unit (7b) with respect to the total structural units constituting the fluorine-containing polymer (E) is preferably 0 mol % to 90 mol %, more preferably 5 mol % to 85 mol %, and still more preferably 10 mol % to 80 mol %. When the proportion of the structural unit (7b) falls within the above range, the degree of a decrease of the dynamic contact angle on the surface of the resist film formed from the photoresist composition in a development with an alkali may be reduced.

Structural Unit (Ec)

The fluorine-containing polymer (E) may have, in addition to the structural units (Ea) and (Eb), a structural unit that includes an acid-labile group (hereinafter, may be also referred to as "structural unit (Ec)") (except for those corresponding to the structural unit (Eb)). When the fluorine-containing polymer (E) has the structural unit (Ec), the configuration of the resulting resist pattern may be more favorable. Examples of the structural unit (Ec) include the structural unit (I) mentioned hereinabove in connection with the polymer (A), and the like.

The proportion of the structural unit (Ec) with respect to the total structural units constituting the fluorine-containing polymer (E) is preferably 10 mol % to 90 mol %, more preferably 20 mol % to 85 mol %, still more preferably 30 mol % to 80 mol %, and particularly preferably 50 mol % to 75 mol %. When the proportion of the structural unit (Ec) is less than the lower limit, formation of development defects in the resist pattern may not be sufficiently inhibited. When the proportion of the structural unit (Ec) is greater than the upper limit, the hydrophobicity of the surface of the resulting resist film may be deteriorated.

Other Structural Unit

Also, the fluorine-containing polymer (E) may have, in addition to the structural units described above, other structural unit, such as, for example: a structural unit that includes an alkali-soluble group, a structural unit that includes at least one structure selected from the group consisting of a lactone structure, a cyclic carbonate structure and a sultone structure, a structural unit that includes an alicyclic group, etc. Examples of the alkali-soluble group include a carboxy group, a sulfonamide group, a sulfo group, and the like. Examples of the structural unit that includes at least one structure selected from the group consisting of a lactone structure, a cyclic carbonate structure and a sultone structure include the structural unit (II) mentioned hereinabove in connection with the polymer (A), and the like.

The proportion of the other structural unit with respect to the total structural units constituting the fluorine-containing polymer (E) is typically no greater than 30 mol %, and preferably no greater than 20 mol %. When the proportion of the other structural unit is greater than the upper limit, the pattern formability of the photoresist composition may be deteriorated.

The amount of the fluorine-containing polymer (E) in the photoresist composition with respect to 100 parts by mass of the polymer (A) is preferably 0 to 20 parts by mass, more preferably 0.5 parts by mass to 15 parts by mass, and still more preferably 1 part by mass to 10 parts by mass. When the amount of the fluorine-containing polymer (E) is greater than the upper limit, the pattern formability of the photoresist composition may be deteriorated.

(F) Solvent

The photoresist composition according to the embodiment of the present invention typically contains (F) a solvent. The solvent (F) is not particularly limited as long as it is capable of dissolving or dispersing at least the polymer (A), the acid generator (B) and the acid diffusion control agent (C), as well as the other acid diffusion controller (D) contained as desired, and the like.

The solvent (F) is exemplified by an alcohol solvent, an ether solvent, a ketone solvent, an amide solvent, an ester solvent, a hydrocarbon solvent, and the like.

Examples of the alcohol solvent include:

monohydric alcohol solvents such as methanol, ethanol, n-propanol, iso-propanol, n-butanol, iso-butanol, sec-butanol, tert-butanol, n-pentanol, iso-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethylcyclohexanol, benzyl alcohol and diacetone alcohol;

polyhydric alcohol solvents such as ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol and tripropylene glycol;

polyhydric alcohol partial ether solvents such as ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, propylene glycol monomethyl ether, propylene glycol monoethyl ether, propylene glycol monopropyl ether, propylene glycol monobutyl ether, dipropylene glycol monomethyl ether, dipropylene glycol monoethyl ether and dipropylene glycol monopropyl ether; and the like.

Examples of the ether solvent include:

dialkyl ether solvents such as diethyl ether, dipropyl ether and dibutyl ether;

cyclic ether solvents such as tetrahydrofuran and tetrahydropyran;

aromatic ring-containing ether solvents such as diphenyl ether and anisole (methyl phenyl ether); and the like.

Examples of the ketone solvent include:

linear ketone solvents such as acetone, methyl ethyl ketone, methyl n-propyl ketone, methyl n-butyl ketone, diethyl ketone, methyl iso-butyl ketone, 2-heptanone (methyl n-pentyl ketone), ethyl n-butyl ketone, methyl n-hexyl ketone, di-iso-butyl ketone and trimethylnonanone;

cyclic ketone solvents such as cyclopentanone, cyclohexanone, cycloheptanone, cyclooctanone and methylcyclohexanone;

2,4-pentanedione, acetonylacetone and acetophenone; and the like.

Examples of the amide solvent include:

cyclic amide solvents such as N,N'-dimethylimidazolidinone and N-methylpyrrolidone;

linear amide solvents such as N-methylformamide, N,N-dimethylformamide, N,N-diethylformamide, acetamide, N-methylacetamide, N,N-dimethylacetamide and N-methylpropionamide; and the like.

Examples of the ester solvent include:

acetic acid ester solvents such as methyl acetate, ethyl acetate, n-propyl acetate, iso-propyl acetate, n-butyl acetate, iso-butyl acetate, sec-butyl acetate, n-pentyl acetate, i-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate and n-nonyl acetate;

polyhydric alcohol partial ether acetate solvents such as ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate and dipropylene glycol monoethyl ether acetate;

carbonate solvents such as diethyl carbonate;

glycol diacetate, methoxytriglycol acetate, ethyl propionate, n-butyl propionate, iso-amyl propionate, diethyl oxalate, di-n-butyl oxalate, methyl acetoacetate, ethyl acetoacetate, methyl lactate, ethyl lactate, n-butyl lactate, n-amyl lactate, diethyl malonate, dimethyl phthalate and diethyl phthalate; and the like.

Examples of the hydrocarbon solvent include:

aliphatic hydrocarbon solvents such as n-pentane, iso-pentane, n-hexane, iso-hexane, n-heptane, iso-heptane, 2,2,4-trimethylpentane, n-octane, iso-octane, cyclohexane and methylcyclohexane;

aromatic hydrocarbon solvents such as benzene, toluene, xylene, mesitylene, ethylbenzene, trimethylbenzene, methylethylbenzene, n-propylbenzene, iso-propylbenzene, diethylbenzene, iso-butylbenzene, triethylbenzene, di-iso-propylbenzene and n-amylnaphthalene; and the like.

Among these, an ester solvent and a ketone solvent are preferred, a polyhydric alcohol partial ether acetate solvent and a cyclic ketone solvent are more preferred, and propylene glycol monomethyl ether acetate and cyclohexanone are still more preferred. The photoresist composition may contain one, or two or more types of the solvent (F).

Other Optional Component(s)

The photoresist composition may contain other optional component(s) in addition to the aforementioned components (A) to (F). The other optional component(s) may be exemplified by an uneven distribution accelerator, a surfactant, an alicyclic skeleton-containing compound, a sensitizing agent, and the like. These other optional components each may be used alone, or in combination of two or more types thereof.

Uneven Distribution Accelerator

The uneven distribution accelerator exhibits the effect of more efficiently segregating the fluorine-containing polymer (E) on the surface of the resist film. When the photoresist composition contains the uneven distribution accelerator, the amount of the fluorine-containing polymer (E) added may be reduced as compared with conventional levels. Therefore, the elution of the components from the resist film into a liquid immersion liquid may be further suppressed and/or an exposure through a liquid immersion medium may be carried out at a higher speed by high speed scanning, without deteriorating characteristics such as the rectangularity of a cross-sectional shape, the LWR performance, the resolving ability and the depth of focus; as a result, the hydrophobicity of the surface of the resist film, which inhibits defects attributed to the liquid immersion, e.g., watermark defects, may be enhanced. As an exemplary uneven distribution accelerator having such features, a low molecular weight compound having a relative permittivity of no less than 30 and no greater than 200, and a boiling point at 1 atm of no less than 100° C. may be used. The compound is specifically exemplified by a lactone compound, a carbonate compound, a nitrile compound, a polyhydric alcohol, and the like.

Examples of the lactone compound include γ-butyrolactone, valerolactone, mevalonic lactone, norbornanelactone, and the like.

Examples of the carbonate compound include propylene carbonate, ethylene carbonate, butylene carbonate, vinylene carbonate, and the like.

Examples of the nitrile compound include succinonitrile, and the like.

Examples of the polyhydric alcohol include glycerin, and the like.

The amount of the uneven distribution accelerator in the photoresist composition with respect to 100 parts by mass of the total polymer(s) is preferably 10 parts by mass to 500 parts by mass, more preferably 15 parts by mass to 300 parts by mass, and still more preferably 20 parts by mass to 100 parts by mass.

Surfactant

The surfactant exhibits the effect of improving a coating property, striation, developability, and the like. Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate; and commercially available products such as KP341 (manufactured by Shin-Etsu Chemical Co., Ltd.), Polyflow No. 75 and No. 95 (each manufactured by Kyoeisha Chemical Co., Ltd.), EFTOP EF301, EF303 and EF352 (each manufactured by Tochem Products Co. Ltd.), Megaface F171 and F173 (each manufactured by DIC Corporation), Fluorad FC430 and FC431 (each manufactured by Sumitomo 3M Limited), ASAHI GUARD AG710, Surflon S-382, SC-101, SC-102, SC-103, SC-104, SC-105 and SC-106 (each manufactured by Asahi Glass Co., Ltd.); and the like. The amount of the surfactant in the photoresist composition with respect to 100 parts by mass of the polymer (A) is typically no greater than 2 parts by mass.

Alicyclic Skeleton-Containing Compound

The alicyclic skeleton-containing compound exhibits the effect of improving dry etching resistance, a pattern configuration, adhesiveness to substrate, and the like.

Examples of the alicyclic skeleton-containing compound include:

adamantane derivatives such as 1-adamantanecarboxylic acid, 2-adamantanone and t-butyl 1-adamantanecarboxylate;

deoxycholic acid esters such as t-butyl deoxycholate, t-butoxycarbonylmethyl deoxycholate and 2-ethoxyethyl deoxycholate;

lithocholic acid esters such as t-butyl lithocholate, t-butoxycarbonylmethyl lithocholate and 2-ethoxyethyl lithocholate;

3-[2-hydroxy-2,2-bis(trifluoromethyl)ethyl]tetracyclo[4.4.0.1$^{2,5}$.1$^{7,10}$]dodecane and 2-hydroxy-9-methoxycarbonyl-5-oxo-4-oxa-tricyclo[4.2.1.0$^{3,7}$]nonane; and the like. The amount of the alicyclic skeleton-containing compound in the photoresist composition with respect to 100 parts by mass of the polymer (A) is typically no greater than 5 parts by mass.

Sensitizing Agent

The sensitizing agent exhibits the action of increasing the amount of an acid generated from the acid generating agent (B) and the like, and exerts the effect of improving "apparent sensitivity" of the photoresist composition.

Examples of the sensitizing agent include carbazoles, acetophenones, benzophenones, naphthalenes, phenols, biacetyl, eosin, rose bengal, pyrenes, anthracenes, phenothiazines, and the like. These sensitizing agents may be used either alone, or in combination of two or more types thereof. The amount of the sensitizing agent in the photoresist composition with respect to 100 parts by mass of the polymer (A) is typically no greater than 2 parts by mass.

Preparation Method of Photoresist Composition

The photoresist composition according to the embodiment of the present invention may be prepared, for example, by mixing the polymer (A), the acid generator (B) and the acid diffusion control agent (C), as well as the optional component(s) and the solvent (F) each contained as needed in a predetermined ratio. After the mixing, the photoresist composition is preferably filtered through a filter with a pore size of about 0.2 μm, for example. The solid content concentration of the photoresist composition is typically 0.1% by mass to 50% by mass, preferably 0.5% by mass to 30% by mass, and more preferably 1% by mass to 20% by mass.

Resist Pattern-Forming Method

A resist pattern forming method according to another embodiment of the present invention includes:

providing a resist film using the photoresist composition according to the embodiment of the present invention (hereinafter, may be also referred to as "resist film-providing step");

exposing the resist film (hereinafter, may be also referred to as "exposure step"); and developing the resist film exposed (hereinafter, may be also referred to as "development step").

According to the resist pattern-forming method, since the aforementioned photoresist composition is used, a resist pattern can be formed that exhibits superior rectangularity of a cross-sectional shape, decreased LWR and a superior resolving ability, while attaining a greater depth of focus. Hereinafter, each step will be explained.

Resist Film-Providing Step

In the resist film-providing step, the photoresist composition according to the embodiment of the present invention is coated on a substrate by appropriate coating means such as spin-coating, cast coating and roll coating to provide a resist film. Examples of the substrate include silicon wafers, wafers covered with silicon dioxide or an antireflective film, and the like. Specifically, after the photoresist composition is coated such that the resulting resist film has a predetermined film thickness, prebaking (PB) is carried out to permit the solvent present in the coating film to be volatilized, resulting in the formation of the resist film. The temperature of PB is typically 60° C. to 140° C., and preferably 80° C. to 120° C. The time period of PB is typically 5 sec to 600 sec, and preferably 10 sec to 300 sec.

Exposure Step

In the exposure step, the resist film provided in the resist film-providing step is exposed. The exposure is carried out, for example, by irradiating the resist film with an exposure light through a photomask (through a liquid immersion medium such as water, as needed). The exposure light is exemplified by: an electromagnetic wave such as a visible light ray, an ultraviolet ray, a far ultraviolet ray, an X-ray and a γ-ray; a charged particle ray such as an electron beam and an α-ray; and the like, in accordance with the line width of the intended pattern. Among these, a far ultraviolet ray and an electron beam are preferred, an ArF excimer laser beam (wavelength: 193 nm), a KrF excimer laser beam (wavelength: 248 nm) and an electron beam are more preferred, and an ArF excimer laser beam and an electron beam are still more preferred.

It is preferred that post exposure baking (PEB) is carried out after the exposure, to facilitate the dissociation of the acid-labile group of the polymer (A) which is mediated by the acid generated from the acid generator (B) at exposed sites of the resist film upon the exposure. This PEB makes the difference of the solubility in a developer solution between at a site subjected to the exposure (light-exposed site) and a site not subjected to the exposure (light-unexposed site). The temperature of the PEB is typically 50° C. to 180° C., and preferably 80° C. to 130° C. The time period of the PEB is typically 5 sec to 600 sec, and preferably 10 sec to 300 sec.

Development Step

In the development step, the resist film exposed is developed with a developer solution to form a predetermined resist pattern. After the development, washing with a rinse agent such as water or an alcohol followed by drying is typically carried out.

In the case of a development with an alkali, examples of the developer solution include aqueous alkali solutions prepared by dissolving at least one type of alkaline compounds such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide (TMAH), pyrrole, piperidine, choline, 1,8-diazabicyclo-[5.4.0]-7-undecene and 1,5-diazabicyclo-[4.3.0]-5-nonene; and the like. Among these, an aqueous TMAH solution is preferred, and a 2.38% by mass aqueous TMAH solution is more preferred.

Alternatively, in the case of a development with an organic solvent, the developer solution is exemplified by: an organic solvent such as a hydrocarbon solvent, an ether solvent, an ester solvent, a ketone solvent and an alcohol solvent; and a solvent containing an organic solvent. Examples of the organic solvent include one, or two or more types of the solvents enumerated in connection with the solvent (F) which may be contained in the abovementioned photoresist composition, and the like. Among these, an ester solvent and a ketone solvent are preferred. As the ester solvent, acetic acid ester solvents are preferred, and n-butyl acetate is more preferred. As the ketone solvent, linear ketones are preferred, and 2-heptanone is more preferred.

In addition, in a case where an exposure through a liquid immersion medium is carried out, a liquid immersion liquid-insoluble protective film for liquid immersion may be provided on the resist film for the purpose of avoiding a direct contact of the resist film with a liquid immersion liquid before the exposure step. As the protective film for liquid immersion, any one of a solvent-peelable protective film that is peeled by a solvent before the development step (see, for example, Japanese Unexamined Patent Application, Publication No. 2006-227632) and a developer solution-peelable protective film that is peeled concomitantly with the development in the development step (see, for example, WO 2005-069076 and WO 2006-035790) may be used. However, a developer solution-peelable protective film for liquid immersion is preferably used in light of throughput.

Acid Diffusion Control Agent

An acid diffusion control agent according to still another embodiment of the present invention contains the compound (1). The compound (1) is represented by the above formula (1).

In the above formula (1), $R^1$, $R^2$ and $R^3$ each independently represent a hydrogen atom or a monovalent hydrocarbon group having 1 to 10 carbon atoms, wherein in a case where the monovalent hydrocarbon group is present in a plurality of number, at least two of these hydrocarbon groups optionally taken together represent a ring structure by binding with each other, together with the carbon atom to which the at least two of these hydrocarbon groups bond; A represents a group having a valency of n that is obtained by combining: at least one group selected from the group consisting of a hydrogen atom, a linear hydrocarbon group having 1 to 30 carbon atoms and an alicyclic hydrocarbon group having 3 to 30 carbon atoms; at least one group selected from the group consisting of —O—, —CO—, —COO—, —SO$_2$O—, —NR—, —NRSO$_2$—, —NRSO$_2$O— and —NRCO—; and n nitrogen atoms as a binding site to the carbonyl group in the above formula (1), wherein a sum of atomic masses of the atoms constituting A is no less than 120, wherein a part or all of hydrogen atoms included in the linear hydrocarbon group and the alicyclic hydrocarbon group are unsubstituted or substituted with a fluorine atom-free group, and wherein R represents a hydrogen atom or a monovalent hydrocarbon group having 1 to 10 carbon atoms; and n is an integer of 1 to 4.

The compound (1) is preferably the compound (2).

In the above formula (2), $R^1$, $R^2$, $R^3$ and n are as defined in the above formula (1); $R^4$ represents a hydrogen atom or a monovalent hydrocarbon group having 1 to 10 carbon atoms; $R^5$ represents a divalent hydrocarbon group having 1 to 10 carbon atoms, wherein $R^4$ and $R^5$ optionally taken together represent an alicyclic structure by binding with each other, together with the nitrogen atom to which $R^4$ and $R^5$ bond; $R^6$ represents a group having a valency of n that is obtained by combining: at least one group selected from the group consisting of a hydrogen atom, a linear hydrocarbon group having 1 to 30 carbon atoms and an alicyclic hydrocarbon group having 3 to 30 carbon atoms; and at least one group selected from the group consisting of —O—, —CO—, —COO—, —SO$_2$O—, —NR—, —NRSO$_2$—, —NRSO$_2$O— and —NRCO—, wherein a part or all of hydrogen atoms included in the linear hydrocarbon group and the alicyclic hydrocarbon group are unsubstituted or substituted with a fluorine atom-free group, wherein R represents a hydrogen atom or a monovalent hydrocarbon group having 1 to 10 carbon atoms, and wherein in the formula (2), a value obtained by the formula of: {[(a formula mass of $R^4$)+(a formula mass of $R^5$)+(an atomic mass of nitrogen)]×n+(a formula mass of $R^6$)} is no less than 120.

The compound (2) is preferably the compound (3).

In the above formula (3), $R^1$ to $R^5$ are as defined in the above formula (2); $R^7$, $R^8$ and $R^9$ each independently represent at least one group selected from the group consisting of a hydrogen atom, a linear hydrocarbon group having 1 to 30 carbon atoms and an alicyclic hydrocarbon group having 3 to 30 carbon atoms, or a group that is obtained by combining: the at least one group selected from the group consisting of a hydrogen atom, a linear hydrocarbon group having 1 to 30 carbon atoms and an alicyclic hydrocarbon group having 3 to 30 carbon atoms; and at least one group selected from the group consisting of —O—, —CO—, —COO—, —SO$_2$O—, —NR—, —NRSO$_2$—, —NRSO$_2$O— and —NRCO—, wherein at least two of $R^7$, $R^8$ and $R^9$ optionally taken together represent a ring structure by binding with each other, together with the carbon atom to which the at least two of $R^7$, $R^8$ and $R^9$ bond; and X represents —O—, —CO—, —COO—, —SO$_2$O—, —NR—, —NRSO$_2$—, —NRSO$_2$O— or —NRCO—, and wherein a sum of formula masses of $R^4$, $R^5$, X, $R^7$, $R^8$ and $R^9$ and atomic masses of the nitrogen and the carbon in the formula (3) is no less than 120.

The acid diffusion control agent according to the embodiment of the present invention has been explained in connection with the acid diffusion control agent (C) contained in the photoresist composition.

Compound

A compound according to yet still another embodiment of the present invention is represented by the above formula (3).

In the above formula (3), $R^1$, $R^2$ and $R^3$ each independently represent a hydrogen atom or a monovalent hydrocarbon group having 1 to 10 carbon atoms, wherein in a case where the monovalent hydrocarbon group is present in a plurality of number, at least two of these hydrocarbon groups optionally taken together represent a ring structure by binding with each other, together with the carbon atom to which the at least two of these hydrocarbon groups bond; $R^4$ represents a hydrogen atom or a monovalent hydrocarbon group having 1 to 10 carbon atoms; $R^5$ represents a divalent hydrocarbon group having 1 to 10 carbon atoms, wherein $R^4$ and $R^5$ optionally taken together represent an alicyclic structure by binding with each other, together with the nitrogen atom to which $R^4$ and $R^5$ bond; $R^7$, $R^8$ and $R^9$ each independently represent at least one group selected from the group consisting of a hydrogen atom, a linear hydrocarbon group having 1 to 30 carbon atoms and an alicyclic hydrocarbon group having 3 to 30 carbon atoms, or a group that is obtained by combining: the at least one group selected from the group consisting of a hydrogen atom, a linear hydrocarbon group having 1 to 30 carbon atoms and an alicyclic hydrocarbon group having 3 to 30 carbon atoms; and at least one group selected from the group consisting of —O—, —CO—, —COO—, —SO$_2$O—, —NR—, —NRSO$_2$—, —NRSO$_2$O— and —NRCO—, wherein at least two of $R^7$, $R^8$ and $R^9$ optionally taken together represent a ring structure by binding with each other, together with the carbon atom to which the at least two of $R^7$, $R^8$ and $R^9$ bond; and X represents —O—, —CO—, —COO—, —SO$_2$O—, —NR—, —NRSO$_2$—, —NRSO$_2$O— or —NRCO—, and wherein a sum of formula masses of $R^4$, $R^5$, X, $R^7$, $R^8$ and $R^9$ and atomic masses of the nitrogen and the carbon in the formula (3) is no less than 120.

The compound according to the embodiment of the present invention is the aforementioned compound (i), and has been explained in the section of the acid diffusion control agent (C) in connection with the photoresist composition.

EXAMPLES

Hereinafter, the present invention is explained in detail by way of Examples, but the present invention is not in any way limited by Examples. Measuring methods for various types of physical properties are shown below.

$^1$H-NMR Analysis and $^{13}$C-NMR Analysis $^1$H-NMR analysis and $^{13}$C-NMR analysis of the compound, as well as $^{13}$C-NMR analysis for the determination of the proportion of each constituent unit and the content of fluorine atoms of the polymer were carried out using a nuclear magnetic resonance spectrometer (JNM-ECX400, manufactured by JEOL, Ltd.).

Synthesis of Compound (i)

Compounds (i-1) to (i-4), which fell under the compound (i), were synthesized in accordance with the following reaction scheme.

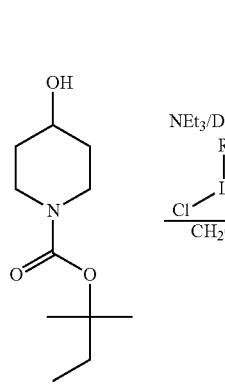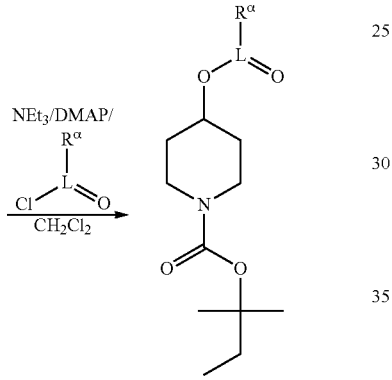

In the above scheme: L represents C and $R^\alpha$ represents an adamantyl group, an ethoxycarbonylmethyl group or a camphor group; or L represents S=O and $R^\alpha$ represents a methyl group.

Example 1

Into a 200 mL eggplant-shaped flask were charged 3.00 g (13.9 mmol) of N-t-amyloxycarbonyl-4-hydroxypiperidine, 2.11 g (20.9 mmol) of triethylamine, 0.034 g of dimethylaminopyridine (0.279 mmol) and 40 g of dichloromethane, and the mixture was cooled to 0° C. on an ice bath. Next, to this mixture, 3.32 g (16.7 mmol) of 1-adamantylcarboxylic acid chloride dissolved in 20 g of dichloromethane was added dropwise over 10 min. Thereafter, the mixture was stirred at 0° C. for 30 min, and then stirred at room temperature for 20 hrs. After the reaction was quenched by the addition of water, the reaction mixture was extracted with dichloromethane, followed by washing with water and purification by way of column chromatography to obtain 4.62 g of a compound represented by the following formula (i-1) (hereinafter, may be also referred to as "compound (i-1)") (yield: 87.8%).

Examples 2 to 4

Compounds represented by the following formulae (i-2) to (i-4) were each synthesized in a similar manner to Example 1 except that the corresponding other derivative was used in place of 1-adamantylcarboxylic acid chloride.

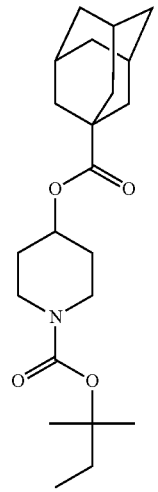

(i-1)

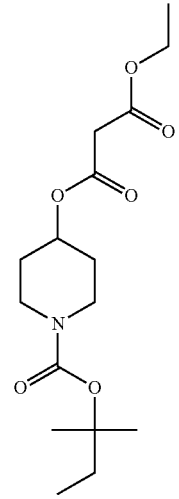

(i-2)

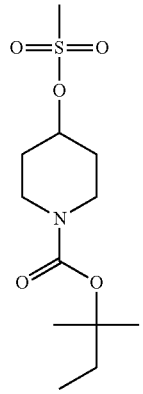

(i-3)

-continued (i-4)

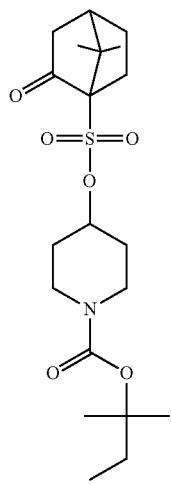

Synthesis of Polymer

Monomers used in the synthesis of the polymer (A) and the fluorine-containing polymer (E) are shown below.

(M-1)

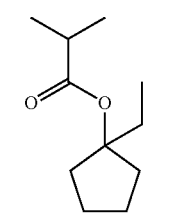

(M-2)

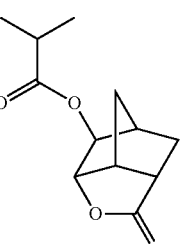

(M-3)

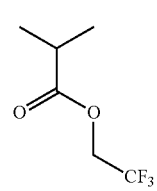

(M-4)

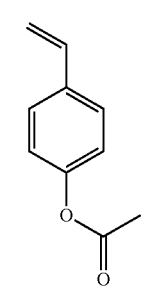

-continued (M-5)

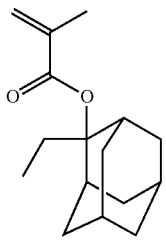

Synthesis of Polymer (A)

Synthesis Example 1

A monomer solution was prepared by dissolving 9.01 g (50 mol %) of the compound (M-1) and 10.99 g (50 mol %) of the compound (M-2) in 40 g of 2-butanone, and further dissolving therein 0.81 g (5 mol % with respect to the total mol number of the compounds) of AIBN as a polymerization initiator. A 100 mL three-neck flask containing 20 g of 2-butanone was purged with a nitrogen gas for 30 min, and then heated to 80° C. with stirring, and the monomer solution prepared above was added dropwise over 3 hrs using a dropping funnel. The time of the start of the dropwise addition was regarded as the time of the start of the polymerization reaction, and the polymerization reaction was allowed to proceed for 6 hrs. After the completion of the polymerization reaction, the polymerization reaction solution was water-cooled to 30° C. or below. The cooled polymerization reaction solution was poured into 400 g of methanol, and the deposited white powder was filtered off. The filtered white powder was washed twice with 80 g of methanol, followed by filtration, and dried at 50° C. for 17 hrs to obtain a polymer (A-1) as a white powder (recovered amount: 15.6 g; yield: 78%). The polymer (A-1) had an Mw of 7,200 and an Mw/Mn of 1.52. The result of $^{13}$C-NMR analysis indicated that the proportions of the structural unit derived from the compound (M-1) and the structural unit derived from (M-2) were 50.2 mol % and 49.8 mol %, respectively. The content of low molecular weight components in the polymer (A-1) was 0.04% by mass.

Synthesis Example 2

After 55.0 g (65 mol %) of the compound (M-4), 45.0 g (35 mol %) of the compound (M-5), 4 g of AIBN and 1 g of t-dodecyl mercaptan were dissolved in 100 g of propylene glycol monomethyl ether, the polymerization was allowed to proceed for 16 hrs under a nitrogen atmosphere, while maintaining the reaction temperature of 70° C. After the completion of the polymerization reaction, the polymerization reaction solution was added dropwise to 1,000 g of n-hexane to solidify and purify the polymer. Next, 150 g of propylene glycol monomethyl ether was added to the polymer, then 150 g of methanol, 34 g of triethylamine and 6 g of water were further added, and a hydrolysis reaction was allowed to proceed for 8 hrs while the mixture was refluxed at the boiling point thereof. After the completion of the reaction, the solvent and triethylamine were distilled under vacuum. The resulting polymer was dissolved in 150 g of acetone, and the solution was added dropwise to 2,000 g of water to permit solidification. The formed white powder was filtered off, and dried at 50° C. for 17 hrs to obtain a polymer (A-2) as a white powder (65.7 g; yield: 76.6%). The polymer (A-2) had an Mw of 10,000 and an Mw/Mn of 2.1. The result of $^{13}$C-NMR analysis indicated that the proportions of the structural unit derived from p-hydroxystyrene and the structural unit derived from the compound (M-5) were 65.4 mol % and 34.6 mol %, respectively. The content of low molecular weight components in the polymer (A-2) was 0.05% by mass.

Synthesis of Fluorine-Containing Polymer (E)

Synthesis Example 3

A monomer solution was prepared by dissolving 79.9 g (70 mol %) of the compound (M-1) and 20.91 g (30 mol %) of the compound (M-3) in 100 g of 2-butanone, and further dissolving 4.77 g of dimethyl 2,2'-azobisisobutyrate as a polymerization initiator. A 1,000 mL three-neck flask containing 100 g of 2-butanone was purged with nitrogen gas for 30 min, and then heated to 80° C. with stirring, and the monomer solution prepared above was added dropwise over 3 hrs using a dropping funnel. The time of the start of the dropwise addition was regarded as the time of the start of the polymerization reaction, and the polymerization reaction was allowed to proceed for 6 hrs. After the completion of the polymerization reaction, the polymerization reaction solution was water-cooled to 30° C. or below. The polymerization reaction solution was transferred to a 2 L separatory funnel, and then the polymerization reaction solution was homogeneously diluted with 150 g of n-hexane. Into the diluted polymerization reaction solution was charged 600 g of methanol and mixed therewith, then 30 g of distilled water was charged, followed by further stirring, and then the mixture was left to stand for 30 min. Thereafter, the underlayer was recovered, and the solvent was substituted to prepare a propylene glycol monomethyl ether acetate solution of a polymer (E-1) (yield: 60%). The polymer (E-1) had an Mw of 7,200 and an Mw/Mn of 2.00. The result of $^{13}$C-NMR analysis indicated that the proportions of the structural unit derived from the compound (M-1) and the structural unit derived from the compound (M-3) were 71.1 mol % and 28.9 mol %, respectively. The content of low molecular weight components in the polymer (E-1) was 0.07% by mass.

Preparation of Photoresist Composition

Components used in the preparation of the photoresist composition are shown below.

(B) Acid Generating Agent triphenylsulfonium 2-(adamantan-1-yl)-1,1-difluoroethane-1-sulfonate (compound represented by the following formula (B-1))

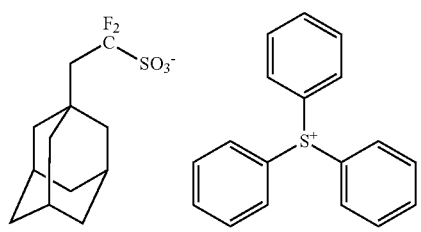

(B-1)

(C) Acid Diffusion Control Agent

C-1: compound (i-1) synthesized above (compound represented by the above formula (i-1))

C-2: compound (i-2) synthesized above (compound represented by the above formula (i-2))

C-3: compound (i-3) synthesized above (compound represented by the above formula (i-3))

C-4: compound (i-4) synthesized above (compound represented by the above formula (i-4))

CC-1: N-t-amyloxycarbonyl-4-hydroxypiperidine (compound represented by the following formula (CC-1))

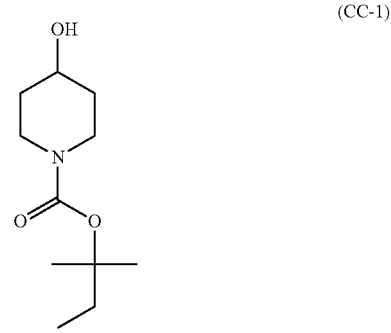

(CC-1)

(F) Solvent

F-1: propylene glycol monomethyl ether acetate

F-2: cyclohexanone (G) Uneven Distribution Accelerator

G-1: γ-butyrolactone

Preparation of Photoresist Composition for Exposure by Way of ArF Excimer Laser Beam Example 5

A photoresist composition (J-1) was prepared by mixing 100 parts by mass of (A-1) as the polymer (A), 8.5 parts by mass of (B-1) as the acid generating agent (B), 30 mol % (mol % with respect to the acid generating agent (B)) of (C-1) as the acid diffusion control agent (C), 3 parts by mass of (E-1) as the fluorine atom-containing polymer (E), 2,240 parts by mass of (F-1) and 960 parts by mass (F-2) as the solvent (F), as well as 30 parts by mass of (G-1) as the uneven distribution accelerator (G).

Examples 6 to 8 and Comparative Example 1

Photoresist compositions (J-2) to (J-4) and (CJ-1) were prepared in a similar manner to Example 5 except that the type and the content of each component were as specified in Table 1.

TABLE 1

| | Photoresist Composition | (A) Polymer type | (A) Polymer amount (parts by mass) | (B) Acid generating agent type | (B) Acid generating agent amount (parts by mass) | (C) Acid diffusion control agent type | (C) Acid diffusion control agent amount (mol %) | (E) Fluorine atom-containing polymer type | (E) Fluorine atom-containing polymer amount (parts by mass) | (F) Solvent type | (F) Solvent amount (parts by mass) | (G) Uneven distribution accelerator type | (G) Uneven distribution accelerator amount (parts by mass) |
|---|---|---|---|---|---|---|---|---|---|---|---|---|---|
| Example 5 | J-1 | A-1 | 100 | B-1 | 8.5 | C-1 | 30 | E-1 | 3 | F-1/F-2 | 2,240/960 | G-1 | 30 |
| Example 6 | J-2 | A-1 | 100 | B-1 | 8.5 | C-2 | 30 | E-1 | 3 | F-1/F-2 | 2,240/960 | G-1 | 30 |
| Example 7 | J-3 | A-1 | 100 | B-1 | 8.5 | C-3 | 30 | E-1 | 3 | F-1/F-2 | 2,240/960 | G-1 | 30 |
| Example 8 | J-4 | A-1 | 100 | B-1 | 8.5 | C-4 | 30 | E-1 | 3 | F-1/F-2 | 2,240/960 | G-1 | 30 |
| Comparative Example 1 | CJ-1 | A-1 | 100 | B-1 | 8.5 | CC-1 | 30 | E-1 | 3 | F-1/F-2 | 2,240/960 | G-1 | 30 |

Formation of Resist Pattern Through Exposure by Way of ArF Excimer Laser Beam

Development with Alkali

An underlayer antireflective film having a film thickness of 105 nm was provided on the surface of a 12-inch silicon wafer by coating a composition for forming an underlayer antireflective film (ARC66, manufactured by Brewer Science) on the surface of the 12-inch silicon wafer using a spin coater (CLEAN TRACK ACT12, manufactured by Tokyo Electron Limited), and thereafter heating the same to 205° C. for 60 sec. Each photoresist composition was coated on the underlayer antireflective film using the spin coater, and subjected to PB at 90° C. で 60 sec. Thereafter, cooling was carried out at 23° C. for 30 sec to provide a resist film having a film thickness of 90 nm. Next, the resist film was exposed using an ArF excimer laser Immersion Scanner (NSR-S610C, manufactured by NIKON) through a 40 nm line-and-space (1L1S) mask pattern, under optical conditions involving NA of 1.3 and dipole (Sigma: 0.977/0.782). After the exposure, PEB was carried out at 90° C. for 60 sec. Thereafter, a development with a 2.38% by mass aqueous TMAH solution was carried out, followed by washing with water and drying to form a positive resist pattern.

Development with Organic Solvent

A negative resist pattern was formed in a similar manner to the abovementioned "Development with Alkali" except that n-butyl acetate was used in place of the 2.38% by mass aqueous TMAH solution as the developer solution and the step of washing with water was skipped.

Evaluations

The photoresist compositions were evaluated through measurements for resist patterns formed therefrom. The results of the evaluations are shown in Table 2. The symbol "-" in Table 2 indicates a reference for evaluation. A scanning electron microscope (S-9380, manufactured by Hitachi High-Technologies Corporation) was used in the measurement of the resist patterns.

LWR Performance

The resist pattern formed was observed from above the pattern using the scanning electron microscope. The line width was measured at arbitrary points of 50 in total, and a 3 Sigma value was determined from the distribution of the measurements, and the value was designated as "LWR performance". The smaller value indicates a more favorable LWR performance. The LWR performance was evaluated to be "A" (favorable) in the case of an improvement of the LWR performance by no less than 10% as compared with the photoresist composition according to Comparative Example 1 (which means a value indicative of the LWR performance being no greater than 90% of a value for the photoresist composition according to Comparative Example 1) being found, and to be "B" (unfavorable) in the case of an improvement of the LWR performance by less than 10% being found.

Resolving Ability

A dimension of the minimum resist pattern which was resolved at an optimum exposure dose was designated as "resolving ability". The smaller value indicates a more favorable resolving ability. The resolving ability was evaluated to be "A" (favorable) in the case of an improvement of the resolving ability by no less than 10% as compared with the photoresist composition according to Comparative Example 1 (which means a value indicative of the resolving ability being no greater than 90% of a value for the photoresist composition according to Comparative Example 1) being found, and to be "B" (unfavorable) in the case of an improvement of the resolving ability by less than 10% being found.

Rectangularity of Cross-Sectional Shape

The cross-sectional shape of the resist pattern which was resolved at the optimum exposure dose was observed, and a line width Lb in the middle portion of the resist pattern and a line width La at the top of the resist pattern were measured. The rectangularity of the cross-sectional shape was evaluated to be "A" (favorable) in a case where the La/Lb value fell within a range of no less than 0.9 and no greater than 1.1, and to be "B" (unfavorable) in a case where the La/Lb value was less than 0.9 or greater than 1.1.

Depth of Focus

On the resist pattern which was resolved at the optimum exposure dose, the dimension when the focus was shifted along the depth direction was observed, and a latitude of the depth direction in which the pattern dimension fell within the range of 90% to 110% of the reference while not accompanied by a bridge and/or residue was measured, and the measurement result was defined as the "depth of focus". The greater value indicates a more favorable depth of focus. The depth of focus was evaluated to be "A" (favorable) in the case of an improvement of the depth of focus by no less than 10% as compared with the photoresist composition according to Comparative Example 1 (which means a value indicative of the depth of focus being no less than 110% of a value for the photoresist composition according to Comparative Example 1) being found, and to be "B" (unfavorable) in the case of an improvement of the depth of focus by less than 10% being found.

TABLE 2

| | | Evaluation results | | | | | | | |
|---|---|---|---|---|---|---|---|---|---|
| | | development with alkali | | | | development with organic solvent | | | |
| | Photoresist composition | LWR performance | resolving ability | rectangularity of cross-sectional shape | depth of focus | LWR performance | resolving ability | rectangularity of cross-sectional shape | depth of focus |
| Example 5 | J-1 | A | A | A | A | A | A | A | A |
| Example 6 | J-2 | A | A | A | A | A | A | A | A |
| Example 7 | J-3 | A | A | A | A | A | A | A | A |
| Example 8 | J-4 | A | A | A | A | A | A | A | A |
| Comparative Example 1 | CJ-1 | — | — | B | — | — | — | B | — |

Preparation of Photoresist Composition for Exposure by Way of Electron Beam

Example 9

A photoresist composition (J-5) was prepared by mixing 100 parts by mass of (A-2) as the polymer (A), 20 parts by mass of (B-1) as the acid generating agent (B), 30 mol % (molar ratio with respect to the acid generating agent (B)) of (C-1) as the acid diffusion control agent (C) as well as 4,280 parts by mass of (F-1) and 1,830 parts by mass of (F-2) as the solvent (F).

Examples 10 to 12 and Comparative Example 2

Photoresist compositions (J-6) to (J-8) were prepared in a similar manner to Example 11 except that the type and the content of each component were as specified in Table 3.

Formation of Resist Pattern Through Exposure by Way of Electron Beam

Each photoresist composition shown in Table 3 below was coated on the surface of an 8-inch silicon wafer using a spin coater (CLEAN TRACK ACT8, manufactured by Tokyo Electron Limited), and subjected to PB at 90° C. for 60 sec. Thereafter, cooling was carried out at 23° C. for 30 sec, whereby a resist film having a film thickness of 50 nm was provided. Next, this resist film was irradiated with an electron beam using a simplified electron beam writer (HL800D, manufactured by Hitachi, Ltd., power: 50 KeV, electric current density: 5.0 ampere/cm$^2$). After the irradiation, PEB was carried out at 130° C. for 60 sec. Thereafter, a development was carried out at 23° C. for 30 sec using a 2.38% by mass aqueous TMAH solution as a developer solution, followed by washing with water and drying to form a positive resist pattern.

Evaluations

Evaluations were made on the resist patterns formed in a similar manner to those described in the aforementioned "Formation of Resist Pattern through Exposure by Way of ArF Excimer Laser Beam" (the photoresist composition according to Comparative Example 2 being employed as a reference for each evaluation). The results of the evaluations are collectively shown in Table 3. The symbol "-" in Table 3 indicates a reference for evaluation.

TABLE 3

| | | Composition | | | | | | | | Evaluation results | | |
|---|---|---|---|---|---|---|---|---|---|---|---|---|
| | | (A) polymer | | (B) acid generating agent | | (C) acid diffusion control agent | | (F) solvent | | LWR | | rectangularity |
| | Photoresist composition | type | amount (parts by mass) | type | amount (parts by mass) | type | amount (mol %) | type | amount (parts by mass) | performance | resolving ability | of cross-sectional shape |
| Example 9 | J-5 | A-2 | 100 | B-1 | 20 | C-1 | 30 | F-1/F-2 | 4,280/1,830 | A | A | A |
| Example 10 | J-6 | A-2 | 100 | B-1 | 20 | C-2 | 30 | F-1/F-2 | 4,280/1,830 | A | A | A |
| Example 11 | J-7 | A-2 | 100 | B-1 | 20 | C-3 | 30 | F-1/F-2 | 4,280/1,830 | A | A | A |
| Example 12 | J-8 | A-2 | 100 | B-1 | 20 | C-4 | 30 | F-1/F-2 | 4,280/1,830 | A | A | A |
| Comparative Example 2 | CJ-2 | A-2 | 100 | B-1 | 20 | CC-1 | 30 | F-1/F-2 | 4,280/1,830 | — | — | B |

From the results shown in Tables 2 and 3, it is found that in both cases of the exposure by way of an ArF excimer laser beam and the exposure by way of an electron beam, and also in both cases the development with an alkali and the development with an organic solvent, the photoresist compositions according to Examples enable a resist pattern to be obtained which exhibits superior pattern configuration, decreased LWR and a superior resolving ability, while attaining a greater depth of focus.

INDUSTRIAL APPLICABILITY

The photoresist composition according to the embodiments of the present invention and the resist pattern-forming method using the photoresist composition enable a resist pattern to be formed that exhibits superior rectangularity of a cross-sectional shape, decreased LWR and a superior resolving ability, while attaining a greater depth of focus. The acid diffusion control agent according to the present invention can be suitably used as an acid diffusion control agent component of the photoresist composition. Moreover, the compound according to the present invention can be suitably used as the acid diffusion control agent. Therefore, these can be suitably used in pattern formation involved in the production of semiconductor devices, in which further progress of miniaturization is expected in the future.

The invention claimed is:
1. A photoresist composition comprising:
a polymer comprising an acid-labile group;
a radiation-sensitive acid generator;
a solvent and
an acid diffusion control agent,
wherein the acid diffusion control agent comprising a compound represented by formula (2):

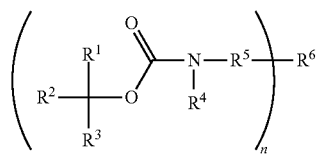

(2)

wherein in the formula (2),
$R^1$, $R^2$ and $R^3$ each independently represent a hydrogen atom or a monovalent hydrocarbon group having 1 to 10 carbon atoms, wherein at least two of the monovalent hydrocarbon groups represented by $R^1$, $R^2$ and $R^3$ optionally join to form a ring structure with the carbon atom to which the at least two of the monovalent hydrocarbon groups bond;
$R^4$ represents a hydrogen atom or a monovalent hydrocarbon group having 1 to 10 carbon atoms;
$R^5$ represents a divalent hydrocarbon group having 1 to 10 carbon atoms, wherein $R^4$ and $R^5$ optionally join to form an alicyclic structure with the nitrogen atom to which $R^4$ and $R^5$ bond;
$R^6$ represents a group having a valency of n that is obtained by combining:
a hydrogen atom, a linear hydrocarbon group having 1 to 30 carbon atoms, an alicyclic hydrocarbon group having 3 to 30 carbon atoms or a combination thereof;
—$SO_2O$—, —NR—, —$NRSO_2$—, —$NRSO_2O$— or —CO—$CH_2$—CO—; and
optionally, —O—, —CO—, —COO—, —$SO_2O$—, —NR—, —$NRSO_2$—, —$NRSO_2O$—, —NRCO— or a combination thereof,
wherein a part or all of hydrogen atoms included in the linear hydrocarbon group and the alicyclic hydrocarbon group are unsubstituted or substituted with a fluorine atom-free group, and R represents a hydrogen atom or a monovalent hydrocarbon group having 1 to 10 carbon atoms, and in the formula (2), a value obtained by a formula of: $\{(F^4+F^5+F^N) \times n+F^6\}$ is no less than 120, wherein $F^4$ represents a formula mass of $R^4$, $F^5$ represents a formula mass of $R^5$, $F^N$ represents an atomic mass of nitrogen, and $F^6$ represents a formula mass of $R^6$; and
n is an integer of 1 to 4.

2. The photoresist composition according to claim 1, wherein the compound represented by the formula (2) is represented by formula (3):

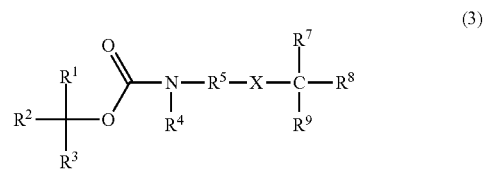

(3)

wherein in the formula (3),
$R^1$, $R^2$ and $R^3$ each independently represent a hydrogen atom or a monovalent hydrocarbon group having 1 to 10 carbon atoms, wherein at least two of the monovalent hydrocarbon groups represented by $R^1$, $R^2$ and $R^3$ optionally join to form a ring structure with the carbon atom to which the at least two of the monovalent hydrocarbon groups bond;
$R^4$ represents a hydrogen atom or a monovalent hydrocarbon group having 1 to 10 carbon atoms;
$R^5$ represents a divalent hydrocarbon group having 1 to 10 carbon atoms, wherein $R^4$ and $R^5$ optionally join to form an alicyclic structure together with the nitrogen atom to which $R^4$ and $R^5$ bond;
$R^7$, $R^8$ and $R^9$ each independently represent a hydrogen atom, a linear hydrocarbon group having 1 to 30 carbon atoms, an alicyclic hydrocarbon group having 3 to 30 carbon atoms or a combination thereof, or a group that is obtained by combining:
a hydrogen atom, a linear hydrocarbon group having 1 to 30 carbon atoms, an alicyclic hydrocarbon group having 3 to 30 carbon atoms or a combination thereof; and
—O—, —CO—, —COO—, —$SO_2O$—, —NR—, —$NRSO_2$—, —$NRSO_2O$—, —NRCO— or a combination thereof,
wherein at least two of $R^7$, $R^8$ and $R^9$ optionally join to form a ring structure with the carbon atom to which the at least two of $R^7$, $R^8$ and $R^9$ bond; and
X represents —$SO_2O$—, —NR—, —$NRSO_2$— or —$NRSO_2O$,
wherein a sum of formula masses of $R^4$, $R^5$, X, $R^7$, $R^8$ and $R^9$ and atomic masses of the nitrogen and the carbon in the formula (3) is no less than 120.

3. The photoresist composition according to claim 1, further comprising an acid diffusion controller other than the acid diffusion control agent.

4. The photoresist composition according to claim 1, wherein in the formula (2), the fluorine atom-free group is a cyano group or a nitro group.

5. The photoresist composition according to claim 1, wherein a value obtained by a formula of: $\{(F^4+F^5+F^N)x \ n+F^6\}$ is no less than 200.

6. The photoresist composition according to claim 1, wherein a value obtained by a formula of: $\{(F^4+F^5+F^N)x \ n+F^6\}$ is no less than 290.

7. The photoresist composition according to claim 1, wherein a value obtained by a formula of: $\{(F^4+F^5+F^N)x \ n+F^6\}$ is no greater than 1000.

8. The photoresist composition according to claim 1, wherein a value obtained by a formula of: $\{(F^4+F^5+F^N)x \ n+F^6\}$ is no greater than 500.

9. The photoresist composition according to claim 1, wherein a content of the acid diffusion control agent with respect of the radiation-sensitive acid generator is from 5 mol % to 50 mol %.

10. The photoresist composition according to claim 1, wherein in the formula (2), the fluorine atom-free group is a cyano group or a nitro group.

11. A resist pattern-forming method, comprising:
applying the photoresist composition according to claim 1 on a substrate to provide a resist film on the substrate;
exposing the resist film; and
developing the resist film exposed.

12. An acid diffusion control agent comprising a compound represented by formula (2):

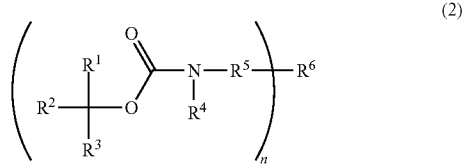

wherein in the formula (2),
$R^1$, $R^2$ and $R^3$ each independently represent a hydrogen atom or a monovalent hydrocarbon group having 1 to 10 carbon atoms, wherein at least two of the monovalent hydrocarbon groups represented by $R^1$, $R^2$ and $R^3$ optionally join to form a ring structure with the carbon atom to which the at least two of the monovalent hydrocarbon groups bond;
$R^4$ represents a hydrogen atom or a monovalent hydrocarbon group having 1 to 10 carbon atoms;
$R^5$ represents a divalent hydrocarbon group having 1 to 10 carbon atoms, wherein $R^4$ and $R^5$ optionally join to form an alicyclic structure with the nitrogen atom to which $R^4$ and $R^5$ bond;
$R^6$ represents a group having a valency of n that is obtained by combining:
a hydrogen atom, a linear hydrocarbon group having 1 to 30 carbon atoms, an alicyclic hydrocarbon group having 3 to 30 carbon atoms or a combination thereof;
—SO$_2$O—, —NR—, —NRSO$_2$—, —NRSO$_2$O— or —CO—CH$_2$—CO—;and
optionally —O—, —CO—, —COO—, —SO$_2$O—, —NR—, —NRSO$_2$—, —NRSO$_2$O—, —NRCO— or a combination thereof,
wherein a part or all of hydrogen atoms included in the linear hydrocarbon group and the alicyclic hydrocarbon group are unsubstituted or substituted with a fluorine atom-free group, and R represents a hydrogen atom or a monovalent hydrocarbon group having 1 to 10 carbon atoms, and in the formula (2), a value obtained by a formula of: $\{(F^4+F^5+F^N)x \ n+F^6\}$ is no less than 120, wherein $F^4$ represents a formula mass of $R^4$, $F^5$ represents a formula mass of $R^5$, $F^N$ represents an atomic mass of nitrogen, and $F^6$ represents a formula mass of $R^6$; and
n is an integer of 1 to 4.

13. The acid diffusion control agent according to claim 12, wherein the compound represented by the formula (2) is represented by formula (3):

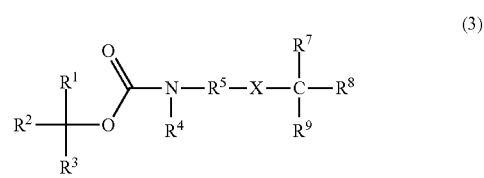

wherein in the formula (3),
$R^1$, $R^2$ and $R^3$ each independently represent a hydrogen atom or a monovalent hydrocarbon group having 1 to 10 carbon atoms, wherein at least two of the monovalent hydrocarbon groups represented by $R^1$, $R^2$ and $R^3$ optionally join to form a ring structure with the carbon atom to which the at least two of the monovalent hydrocarbon groups bond;
$R^4$ represents a hydrogen atom or a monovalent hydrocarbon group having 1 to 10 carbon atoms;
$R^5$ represents a divalent hydrocarbon group having 1 to 10 carbon atoms, wherein $R^4$ and $R^5$ optionally join to form an alicyclic structure with the nitrogen atom to which $R^4$ and $R^5$ bond;
$R^7$, $R^8$ and $R^9$ each independently represent a hydrogen atom, a linear hydrocarbon group having 1 to 30 carbon atoms, an alicyclic hydrocarbon group having 3 to 30 carbon atoms or a combination thereof, or a group that is obtained by combining:
a hydrogen atom, a linear hydrocarbon group having 1 to 30 carbon atoms, an alicyclic hydrocarbon group having 3 to 30 carbon atoms or a combination thereof; and
—O—, —CO—, —COO—, —SO$_2$O—, —NR—, —NRSO$_2$—, —NRSO$_2$O—, —NRCO— or a combination thereof,
wherein at least two of $R^7$, $R^8$ and $R^9$ optionally join to form a ring structure with the carbon atom to which the at least two of $R^7$, $R^8$ and $R^9$ bond; and
X represents —SO$_2$O—, —NR—, —NRSO$_2$— or —NRSO$_2$O—,
wherein a sum of formula masses of $R^4$, $R^5$, X, $R^7$, $R^8$ and $R^9$ and atomic masses of the nitrogen and the carbon in the formula (3) is no less than 120.

14. The acid diffusion control agent according to claim 12, wherein a value obtained by a formula of: $\{(F^4+F^5+F^N)x \ n+F^6\}$ is no less than 200.

15. The acid diffusion control agent according to claim 12, wherein a value obtained by a formula of: $\{(F^4+F^5+F^N)x \ n+F^6\}$ is no less than 290.

16. The acid diffusion control agent according to claim 12, wherein a value obtained by a formula of: $\{(F^4+F^5+F^N)x \ n+F^6\}$ is no greater than 1000.

17. The acid diffusion control agent according to claim 12, wherein a value obtained by a formula of: $\{(F^4+F^5+F^N)\times n+F^6\}$ is no greater than 500.

18. A compound represented by formula (3):

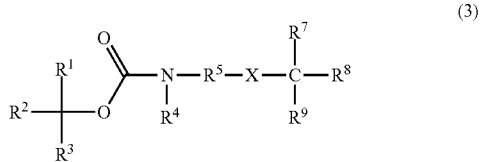

(3)

wherein in the formula (3), $R^1$, $R^2$ and $R^3$ each independently represent a hydrogen atom or a monovalent hydrocarbon group having 1 to 10 carbon atoms, wherein at least two of the monovalent hydrocarbon groups represented by $R^1$, $R^2$ and $R^3$ optionally join to form a ring structure with the carbon atom to which the at least two of the monovalent hydrocarbon groups bond;

$R^4$ represents a hydrogen atom or a monovalent hydrocarbon group having 1 to 10 carbon atoms;

$R^5$ represents a divalent hydrocarbon group having 1 to 10 carbon atoms, wherein $R^4$ and $R^5$ optionally join to form an alicyclic structure with the nitrogen atom to which $R^4$ and $R^5$ bond;

$R^7$, $R^8$ and $R^9$ each independently represent a hydrogen atom, a linear hydrocarbon group having 1 to 30 carbon atoms, an alicyclic hydrocarbon group having 3 to 30 carbon atoms or a combination thereof, or a group that is obtained by combining:

a hydrogen atom, a linear hydrocarbon group having 1 to 30 carbon atoms, an alicyclic hydrocarbon group having 3 to 30 carbon atoms or a combination thereof; and —O—, —CO—, —COO—, —SO$_2$O—, —NR—, —NRSO$_2$—, —NRSO$_2$O—, —NRCO— or a combination thereof, wherein at least two of $R^7$, $R^8$ and $R^9$ optionally join to form a ring structure with the carbon atom to which the at least two of $R^7$, $R^8$ and $R^9$ bond; and X represents —SO$_2$O—, —NR—, —NRSO$_2$— or —NRSO$_2$O—, wherein a sum of formula masses of $R^4$, $R^5$, X, $R^7$, $R^8$ and $R^9$ and atomic masses of the nitrogen and the carbon in the formula (3) is no less than 120.

* * * * *